United States Patent
Bretting

(10) Patent No.: US 6,197,982 B1
(45) Date of Patent: Mar. 6, 2001

(54) VITAMIN D ANALOGUES

(75) Inventor: Claus Aage Svensgaard Bretting, Frederiksberg (DK)

(73) Assignee: Leo Pharmaceutical Products Ltd. A/S, Ballerup (DK)

(*) Notice: Subject to any disclaimer, the term of this patent is extended or adjusted under 35 U.S.C. 154(b) by 0 days.

(21) Appl. No.: 09/202,200

(22) PCT Filed: May 15, 1997

(86) PCT No.: PCT/DK97/00225

§ 371 Date: Dec. 4, 1998

§ 102(e) Date: Dec. 4, 1998

(87) PCT Pub. No.: WO97/46522

PCT Pub. Date: Dec. 11, 1997

(30) Foreign Application Priority Data

Jun. 4, 1996 (GB) .................................... 9611603

(51) Int. Cl.[7] ........................ C07C 401/00; A61K 31/59
(52) U.S. Cl. ........................ 552/653; 514/167; 552/653
(58) Field of Search .............................. 552/653; 514/167

(56) References Cited

U.S. PATENT DOCUMENTS 5,585,369   12/1996   DeLuca et al. ..................... 514/167

FOREIGN PATENT DOCUMENTS

| 296 800 | 12/1988 | (EP) . |
| 93/19044 | 9/1993 | (WO) . |
| 94/10139 | 5/1994 | (WO) . |

Primary Examiner—Sabiha N. Qazi

(74) Attorney, Agent, or Firm—Pillsbury Madison & Sutro LLP

(57) ABSTRACT

The present invention relates to compounds of formula (I), in which formula X is hydrogen or hydroxy; $R^1$ and $R^2$, which may be the same or different, stand for hydrogen or a $C_1$–$C_3$ alkyl radical; or $R^1$ and $R^2$, taken together with the carbon atom bearing the group X, can form a $C_3$–$C_6$ carbocyclic ring, $R^3$ stands for a $C_1$–$C_3$ alkyl radical, an aryl or an aralkyl radical, or for $YR^4$, in which Y stands for the radicals —CO—S—, —CS—O— or —CS—S—, and $R^4$ stands for a $C_1$–$C_3$ alkyl radical or an aryl or an aralkyl radical; Q is $(CH_2)_n$, n being 1–4. $R^1$, $R^2$ and Q independently may optionally be substituted with one or more fluorine atoms. The compounds show strong activity in inducing differentiation and inhibiting undesirable proliferation of certain cells as well as immunomodulating and antiinflammatory effects.

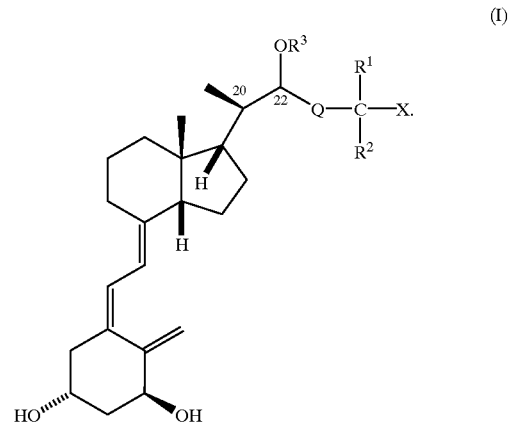

(I)

12 Claims, No Drawings

VITAMIN D ANALOGUES

This application is the national phase of international application PCT/DK97/00225 filed May 5, 1997.

This invention relates to a hitherto unknown class of compounds which shows strong activity in inducing differentiation and inhibiting undesirable proliferation of certain cells, including skin cells and cancer cells, as well as immunomodulating and antiinflammatory effects, to pharmaceutical preparations containing these compounds, to dosage units of such preparations, and to their use in the treatment and/or prophylaxis of diseases characterized by abnormal cell differentiation and/or cell proliferation such as e.g. psoriasis and other disturbances of keratinization, HIV-associated dermatoses, wound healing, cancer, including skin cancer, and of diseases of, or imbalance in, the immune system, such as host versus graft and graft versus host reaction and transplant rejection, and autoimmune diseases, such as discoid and systemic lupus erythematosus, diabetes mellitus and chronic dermatoses of autoimmune type, e.g. scleroderma and pemphigus vulgaris, and inflammatory diseases, such as rheumatoid arthritis and asthma, as well as a number of other disease states including hyperparathyroidism, particularly secondary hyperparathyroidism associated with renal failure, cognitive impairment or senile dementia (Alzheimers disease) and other neurodegenerative diseases, hypertension, acne, alopecia, skin atrophy, e.g. steroid induced skin atrophy, skin ageing, including photo-ageing, and to their use for promoting osteogenesis and treating/preventing osteoporosis and osteomalacia.

The compounds of the invention constitute a novel class of vitamin D analogues and are represented by the general formula I

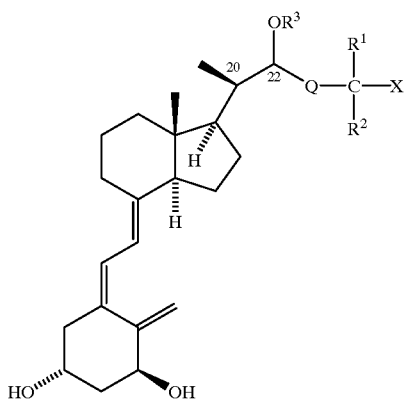

in which formula X is hydrogen or hydroxy; $R^1$ and $R^2$, which may be the same or different, stand for hydrogen or a $C_1$–$C_3$ alkyl radical; or $R^1$ and $R^2$, taken together with the carbon atom bearing the group X, can form a $C_3$–$C_6$ carbocyclic ring; $R^3$ stands for a $C_1$–$C_3$ alkyl radical, an aryl or an aralkyl radical, or for $YR^4$, in which Y stands for the radicals —CO—S—, —CS—O— or —CS—S—, and $R^4$ stands for a $C_1$–$C_3$ alkyl radical or an aryl or an aralkyl radical; Q is $(CH_2)_n$, n being 1–4. $R^1$, $R^2$ and Q independently may optionally be substituted with one or more fluorine atoms.

Examples of $R^1$ and $R^2$ when taken separately include (apart from hydrogen), but are not limited to, methyl, trifluoromethyl, ethyl, pentafluoroethyl, and normal-, iso- and cyclo-propyl.

Examples of $R^1$ and $R^2$ when taken together include di-, tri-, tetra- and pentamethylene.

Examples of $R^3$ and $R^4$ include, but are not limited to, methyl, ethyl, propyl, normal-, iso- and cyclopropyl, phenyl and benzyl.

Most preferred examples of Q include di- and trimethylene.

As can be seen from formula I, depending on the meanings of $R^1$, $R^2$, $R^3$, Q and X the compounds of the invention can comprise several diastereoisomeric forms (e.g. R or S configuration at the carbon atom bearing the radicals $R^1$, $R^2$, and X). The invention covers all these diastereoisomers in pure form as well as mixtures thereof.

In particular, both diastereoisomers having the two possible configurations (in the following designated "A" and "B") at the carbon atom marked "22" are included. A is the preferred one.

In addition, prodrugs of I in which one or more of the hydroxy groups are masked as groups which can be reconverted to hydroxy groups in vivo can also be envisaged.

Compounds of formula I in which X is hydrogen also may act as prodrugs, as these compounds are relatively inactive in vitro but are converted to active compounds of formula I by enzymatic hydroxylation after administration to the patient.

It has been known for more than two decades that vitamin D ($D_3/D_2$) is a pro-hormone which is hydroxylated in vivo to the active hormone 1α,25-dihydroxy-vitamin $D_3$ (1,25 $(OH)_2D_3$ or calcitriol). Vitamin $D_2$ is metabolized in the same way as $D_3$ and is bioequivalent with $D_3$ in humans. 1,25$(OH)_2D_3$ is responsible for maintaining calcium (and phosphate) homeostasis by regulation of the intestinal calcium absorption, the renal calcium excretion and the bone mineralization/resorption. Other hormones such as parathyroid hormone (PTH) and calcitonin function as positive and negative feedback calcium regulators respectively in concert with 1,25$(OH)_2D_3$ [1],[2].

This knowledge has led to the use of 1,25$(OH)_2D_3$ and its prodrug 1α-hydroxy-$D_3$ (alfacalcidol, INN) in the treatment of patients with kidney failure, where the important renal 1α-hydroxylation of 25-hydroxy vitamin D is impaired, leading to hypocalcemia, secondary hyperparathyroidism and bone demineralization (renal osteodystrophy) [1].

It has since been shown that the (nuclear) receptor for 1,25$(OH)_2D_3$ (VDR) is present, not only in the intestine, bone and kidney, but in a large number of other locations, such as e.g. parathyroid glands, islets of the pancreas, mammary gland cells, keratinocytes and fibroblasts of the skin, circulating monocytes and (activated) lymphocytes, and many other normal cell types and tissue; in addition the VDR is also present in several cancer cell lines [2],[3],[4].

In accordance with this widespread occurrence of the VDR, it has been experimentally demonstrated that 1,25 $(OH)_2D_3$ has biological effects over and beyond the "classical" effects on calcium regulation.

It was shown that 1,25$(OH)_2D_3$ is able to stimulate the differentiation of cells and inhibit excessive cell proliferation [5], suggesting potential use in the treatment of e.g. psoriasis and cancer. It was also shown that 1,25$(OH)_2D_3$ influences the effects and/or production of interleukins [6], indicating the potential use of this compound in the treatment of immunological disorders, such as e.g. autoimmune diseases and rejection of transplants.

The use of 1,25$(OH)_2D_3$, or its pro-drug 1α(—OH—$D_3$, for the treatment of several other disease states has also been suggested: hypertension [7], diabetes mellitus [8], alopecia [9], acne [10], osteoporosis [11] and neurodegenerative disorders [12].

The inhibition of angiogenesis by 1,25(OH)$_2$D$_3$[13] indicates a possible inhibition of tumour growth via reduction of the growth of new blood vessels into the tumour.

However, the therapeutic possibilities of 1,25(OH)$_2$D$_3$ in several of these indications are severely limited by the potent effect of this hormone on calcium metabolism, because serious side effects due to hypercalcemia will result from the high doses necessary to obtain a therapeutic effect on e.g. psoriasis or cancer or immunological disorders.

In order to overcome this problem a large number of vitamin D analogues have been described, and some of these show selectivity in favour of the cell differentiation inducing/cell proliferation inhibiting activity as compared with the effect on calcium metabolism [3],[4],[14].

This work has resulted in therapeutically useful, or potentially useful, vitamin D analogues. Thus, the vitamin D$_3$ analogue, MC$_{903}$ (calcipotriol, calcipotriene, INN, cf. table 1), is a potent inducer of cell differentiation and inhibitor of cell proliferation which shows only moderate activity on calcium metabolism in vivo [15].

Calcipotriol is on the market as a safe and effective drug for the treatment of the hyperproliferative disease of the skin, psoriasis. Calcipotriol renders improvement, without hypercalcemia, in 70–80% of the patients ([6],[17]. However, this selectivity is not paralleled by in vitro studies, which show that calcipotriol binds equally well as 1,25(OH)$_2$D$_3$ to the intestinal vitamin D receptor. The low in vivo activity on calcium metabolism of calcipotriol is due to a rapid metabolism of the compound, thus limiting the potential of this compound for systemic use [16].

The efficacy of several vitamin D analogues in inducing differentiation and inhibiting proliferation of cancer cells has been demonstrated, both in vitro and in vivo see e.g. [3], [4], [11], [14], [18], [19], [20], [21], [22], [23].

One such interesting analogue is EB 1089 [22], [24] which inhibits the growth of breast cancer cells in vitro and in vivo [4], [25]. There is a definite selectivity between the anti-cancer and the calcemic effects in vivo, but the molecular basis for this selectivity is not really understood [4]. EB 1089 is presently in clinical study [26].

A promising series of vitamin D analogues having differentiation inducing and antiproliferative activity are the 20-epi-analogues [18], [27], [28] in which the stereochemistry at carbon-20 in the side chain is altered to the "unnatural", so-called 20-epi, configuration. The two most studied of these 20-epi-analogues are KH 1060 (20-epi-22-oxa-25,26,27-trihomo-1,25-(OH)$_2$D$_3$; lexacalcitol, INN) [18], [29] and MC$_{1288}$ (20-epi-1,25(OH)$_2$D$_3$; cf. table 1) [18], [30].

It was found that the change from 20-"normal" to 20-"epi" configuration has a profound and advantageous biological significance. Generally speaking, the most active of these analogues are characterized by their high, or very high, potencies as regulators of cell growth and/or immune responses; their calcemic activity being equivalent to that of 1,25(OH)$_2$D$_3$, or a few times stronger [18].

Separation of immunoregulating activity from calcemic activity has also been demonstrated for some vitamin D analogues [18], [27]. Some important findings concerning the immunological effects of 1,25(OH)$_2$D$_3$ itself will be illustrative of the present state of the art; references to original papers can be found in recent articles, e.g. [27], [31] and [32] (dermatology in particular). 1,25(OH)$_2$D$_3$ stimulates the differentiation of monocytes towards macrophages and enhances their antibacterial activity, and 1,25(OH)$_2$D$_3$ restores normal immune functions in vitamin D deficiency states in vivo. On the other hand 1,25(OH)$_2$D$_3$ has an immunosuppressive effect on the antigen-mediated part of the immune system. The proliferation of activated T-lymphocytes is inhibited with down-regulation of cytokines IL-2 and INF-γ. In vitro this down-regulation leads to an indirect inhibition of the formation of antibodies (IgM and IgG) from B-lymphocytes. Cytotoxic T-cells are also inhibited and regulatory/suppressor T-lymphocytes are stimulated. Some studies also report downregulation by 1,25(OH)$_2$D$_3$ of the production/release of cytokines such as IL-1 and TNF-C from antigen-stimulated monocytes/macrophages.

These findings suggest clinical applications of 1,25(OH)$_2$D$_3$ in the fields of organ or cell transplantations and in autoimmune diseases, but its calcemic effects severely limit its usefulness in clinical practice.

The new vitamin D analogues [18], [27] however, show some promise in this direction, as the following examples will indicate.

The 20-epi-analogue MC$_{1288}$ was effective as an immunosuppressant in a rat model of heart and small bowel transplantations, preventing graft rejection [30]; the serum calcium level was moderately increased.

The 20-epi- and the 20-normal analogues KH 1060 and CB 966 prolonged skin allograft survival in mice [33]. KH 1060 was the most potent immunosuppressor, but induced hypercalcemia in the highest, and most effective, dose. Combination treatment with Cyclosporin A (CyA) was more effective than either agent alone, with moderate rise of serum calcium. MC 1288 and two other 20-epi-analogues were also very effective in this assay [34e] and were less hypercalcemic than KH 1060.

KH 1060 was an effective immunoregulator in the autoimmune disease, type I diabetes, which was studied in the non-obese diabetic (NOD) mouse [35]. The effect on calcium and bone was only slight, in contrast to 1,25(OH)$_2$D$_3$ (which otherwise was an effective immunomodulator, too).

In a related study [36] where the effect of autoimmune memory was studied by the transplantation of completely MHC[1]-matched, or syngeneic, —cells of the islets of the pancreas to NOD mice, both KH 1060 and CyA were very effective in delaying autoimmune disease recurrence, but both were toxic in the most effective high doses. KH 1060 and CyA combined, in lower, nontoxic, doses were as effective as each compound in high dose, and the effect on calcium metabolism was reduced.

[1]major histocompatibility complex

There is recent evidence [37] which indicates that the powerful activity of the 20-epi-analogues KH 1060 and MC$_{1288}$ may be connected with enhanced transcriptional activity, compared to 1,25(OH)$_2$D$_3$, but in vivo there is a long range of other factors, such as e.g. absorption, transport to target cells (binding proteins) and metabolic and cellular uptake properties, that may determine the non-classic versus calcitropic activities of vitamin D analogues [11], [14] (p.301), [20], so that the selection of potential candidates for clinical application cannot solely be based on in vitro screening.

As will be seen from the above description of the present state of the art, the newer vitamin D analogues are quite effective agents for treating psoriasis and they are promising as immunosuppressive and anticancer agents. However, there is still a need for an improved efficacy and a higher safety ratio in respect to the calcitropic side effects.

The compounds of the present invention have new and unexpected advantageous properties, which mean that they are promising agents, possessing increased efficacy or reduced side effects, for treating such pathological states for which 1,25(OH)$_2$D$_3$ or its analogues would be indicated, but for their calcemic (side) effect.

The topic of the relationship between the chemical structure of vitamin D analogues and their biological activity (in vitro or in vivo) has been discussed; for recent reviews see e.g. [3], [21]. For newer analogues from LEO, see [34a–d] and [38a–d]; in these studies systematic structural modifications has been correlated with inhibition of proliferation and induction of differentiation of U 937 leukaemia cells, with calcemic activity in the rat, and with vitamin D receptor binding. The structural modifications include: side chain length and branching [34a–d], [38a–d], do.-unsaturation [34a,b,c], (38c,d], C-20-stereochemistry [34a,b,c], [38b,c], heteroatoms or aromatic rings in the side chain [34b], [38b] and hydroxy or alkoxy substitution at C-20 [34d], C-22 [34c] and C-24 [38c]. It appears that there is frequently very big variation in the activity, even for small structural changes [34a,d], [38b,c]. In most cases there is little relationship between in vitro anti-cancer activity and in vivo calcemic activity, or receptor binding affinity. Some receptor binding is evidently necessary for cell regulating activity [27], but e.g. in the case of 20- and 22-hydroxy/alkoxy substituted analogues, potent anti-cancer activity is compatible with very low receptor binding [34c,d]. Correlations between structure and immunological activity has also been discussed [18], [27]; it is found that some of the 20-epi analogues are potent immunosuppressive agents.

Summarizing this evidence: while it may be possible, within a confined series of very closely related compounds, to some extent to correlate a structural change with the result from a well-known biological assay, it is impossible to make predictions of the activity in a new assay from the chemical structure alone.

Surprisingly, compounds 101 and 102 of the present invention have new and unexpected biological activity in the assays presented in table 1, in which table also the corresponding activities of some closely related reference compounds are included. The calcemic activities of the reference compounds have been described [15], [18], [34c], and also MLR-data for MC 1288 [18], but it is apparent that the potent effects of the compounds of the invention on skin cell proliferation and mixed lymphocyte reaction combined with only moderate calcemic activity could not be predicted from these prior art data.

European patent application 0 296 800, filing date Jun. 21, 1988, discloses compounds which are vitamin D analogues containing a saturated, all carbon, side chain, substituted at position 22 with a hydroxy or a lower alkyloxy group and these compounds are claimed to be useful in the treatment of disease states characterized by metabolic calcium deficiencies or having tumour cell differentiation-inducing activity. Similar compounds are also described in the non-patent literature [39], [40]. They were tested for vitamin D activity, which they did not have, i.e. no significant hypercalcemic effect in rats [39], and for their ability to induce differentiation of HL-60 cancer cells. The most active compound was 22S-methoxy-1,25(OH)$_2$D$_3$ which was 0.25 times as potent as 1,25(OH)$_2$D$_3$ in this assay. The receptor binding affinity of 22S-methoxy-1,25(OH)$_2$D$_3$ was 0.03 times that of 1,25(OH)$_2$D$_3$, [40].

The compounds I of the present invention differ from these prior art compounds by having the above mentioned "unnatural" 20-epi-configuration. This configuration is also present in several other newer vitamin D analogues, among them the compounds disclosed in our previous international patent application number PCT/DK90/00156, filing date Jun. 19, 1990, publication number WO 91/00271, and international patent application number PCT/DK93/00105, filing date Mar. 23, 1993, publication number WO 93/19044, and in Japanese patent application, publication number 7-304733, filing date May 10, 1994. These 20-epi-analogues are stated to have cell differentiation inducing activity etc.

The present compounds I are distinguished from the compounds of PCT/DK90/00156 and Japanese patent application 7-304733 in having an alkyloxy or alkyl(aryl)oxy carbonyloxy (or thio-/dithio-alkyl(aryl)oxy carbonyloxy) substituent in position 22 of the side chain, instead of hydrogen atoms or a hydroxy group or a protected hydroxy group in this position, and are distinguished from the compounds of PCT/DK93/00105 which carry a carbon-carbon triple bond in position 23,24 of the side chain, in having only carbon-carbon single bonds in the side chain. The structural differences of the present compounds I from the related 20-epi vitamin D analogues of the above mentioned patent applications made it possible to achieve new and unexpected advantages, as demonstrated in the biological assays mentioned in the following.

In order to demonstrate the effectiveness of the compounds of formula I of the invention, the information of Table 1 is referred to: in particular columns "HaCaT, rel.", "HaCaT, max. %", "MLR, rel.", and "Calc., rel."; the meaning of which is explained in the following.

A useful assay for the rating of test compounds for antiproliferative activity in skin cells, e. g. antipsoriatic effect, is the in vitro assay using HaCaT, a spontaneously immortalized, non-tumorigenic human skin keratinocyte cell line, [41], measuring $^3$H-thymidine uptake.

An in vitro assay for the rating of test compounds for immunosuppressive potency is the mixed lymphocyte reaction assay, "MLR", measuring the allogeneic stimulation of mouse spleen lymphocytes: lymphocytes, obtained from the spleens of BALB/c and CB6F1 mice, are stimulated by co-cultivating 5×10$^6$/ml cells from BALB/c mice (responders) with 7.5×10$^6$/ml cells from CB6F1 mice (inducers). The mixed cultures of lymphocytes are incubated with the test compounds for 72 hours. Cellular DNA-synthesis is assessed by the incorporation of $^3$H-thymidine in the D Generally, the classical effects of 1,25(OH)$_2$ vitamin D$_3$ on the calcium balance in the organism, including calcemic and calciuric activities, are unwanted in the vitamin D analogues of the present invention, in which selectivity for e.g. inhibition of the proliferation of certain cells and/or immunosuppressive activity is normally desired.

The calcemic activity of the compounds was determined in rats in vivo, as previously described [15]. In table 1, column "Calc., rel.", the calcemic activities of selected compounds (relative to 1,25(OH)$_2$D$_3$) are listed; as mentioned, low values for the compounds of the present invention are ordinarily preferred.

It appears from table 1 that the two selected exemplified compounds, Comp. 101 and Comp. 102 are considerably more potent than 1,25(OH)$_2$D$_3$ in the HaCaT-assay (psoriasis model), while retaining the same, or higher, maximal inhibition at $10^{-7}$ M as $1,25(OH)_2D_3$. In addition the calcemic activity is only about half as large as that of $1,25(OH)_2D_3$.

Concerning the other important property of the compounds I of the invention, their immunosuppressive activity, it is apparent from Table 1, column "MLR, rel.", that the selected Compounds 101 and 102 have potent effects, also in comparison with the prior art reference compounds. Of these, the compound MC1288 is particularly interesting, as it has been demonstrated to have a valuable immunosuppressive activity in animal transplantation experiments [30]. In addition the compounds of the present invention exhibit a favourable ratio between the relative MLR-potency and the relative calcemic activity.

Thus, also when the immunosuppressive properties are considered, less danger of calcemic side effects is to be expected from the present compounds 1, than from those of prior art mentioned in table 1.

TABLE 1

Biological Tests of Compounds I and Reference Compounds

| Side chain at C-17 | Comp. No. | Code No. | HaCaT rel. ¤, ¶ | HaCaT max. % • | MLR rel. ¤, ¶ | Calc. rel. ¤ |
|---|---|---|---|---|---|---|
| (structure: C-17 side chain with methoxy ether and terminal C(CH₃)₂OH) | 101 | | 28 | 92 | 175 | 0.45 |
| (structure: C-17 side chain with ethoxy ether and terminal C(CH₃)₂OH) | 102 | | 137 | 85 | 161 | 0.50 |
| Reference compounds | | | | | | |
| (structure: 1,25(OH)₂D₃ side chain) | | 1,25* | 1 | 85 | 1 | 1 |
| (structure: MC903 side chain with allylic OH and cyclopropyl) | | MC903# | 1.8 | 78 | 0.6 | 0.005 |
| (structure: MC1288 side chain, 20-epi) | | MC1288 | 43 | 76 | 150 | 2.5 |
| (structure: CB1297 side chain with C-22 OH) | | CB1297 | 45 | 75 | 12 | n.d. |
| (structure: GS1535 side chain with OH, alkyne, and ethyl groups) | | GS1535 | 313 | 82 | 13 | 8.2 |

TABLE 1-continued

Biological Tests of Compounds I and Reference Compounds

| Side chain at C-17 o | Comp. No. | Code No. | HaCaT rel. ¤, ¶ | HaCaT max. % • | MLR rel. ¤, ¶ | Calc. rel. ¤ |
|---|---|---|---|---|---|---|
| [structure] | | GS1725 | 4.4 | 96 | 150 | 12 |
| [structure] | | GS1720 | 3.9 | 70 | 36 | 1.2 |

Notes to Table 1
o The rest of the molecule is the same as in formula I. The 22-OH/OMe/OEt compounds are all 22A-isomers.
¤ The values are relative to 1,25 $(OH)_2D_3$; a value greater than 1 indicates a compound which is more active than 1,25 $(OH)_2D_3$ in the assay.
¶ Calculated as the ratio between the $IC_{50}$ value of 1,25 $(OH)_2D_3$ and the $IC_{50}$ value of the compound; $IC_{50}$ being the concentration which results in 50% inhibition of the $^3$H-thymidine incorporation compared to controls.
• "HaCaT, max %" indicates the maximal inhibition of the cell proliferation (maximal efficacy) which is obtainable at the higher concentration of $10^{-7}$ M of a compound.
* 1,25 = 1,25 $(OH)_2D_3$ = 1,25 $(OH)_2$-vitamin-$D_3$.
MC903 = Calcipotriol, (see text above).
n.d. = not determined.

Compounds I can be prepared from the vitamin D-derived aldehyde compound 1 (Scheme 1); a synthesis of which has been reported [42], for example by the routes outlined in Scheme 1.

The following standard abbreviations are used throughout this disclosure: Me=methyl; Et=ethyl; Pr=n-propyl; Bn=benzyl; Ph=phenyl; THP=tetrahydro-4H-pyran-2-yl; TMS=trimethylsilyl; DMAP=4-dimethylaminopyridine; PPTS=pyridinium p-toluenesulfonate; pet.ether=petroleum ether; THF=tetrahydrofuran; TBAF=tetra-(n-butyl)-ammonium fluoride; b.p.=boiling point; PLC=Preparative thin-Layer Chromatography; HPLC=High Performance Liquid Chromatography.

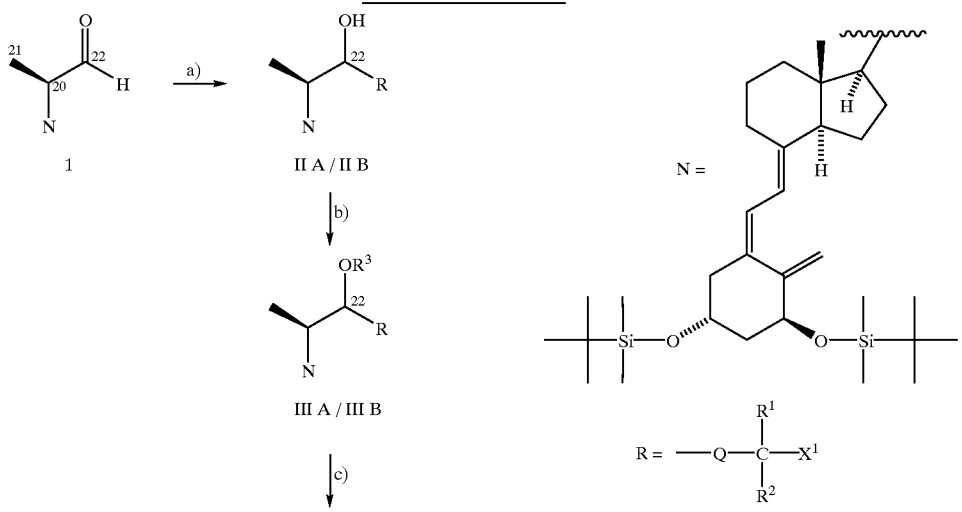

Scheme 1
Synthesis of Compounds I

-continued

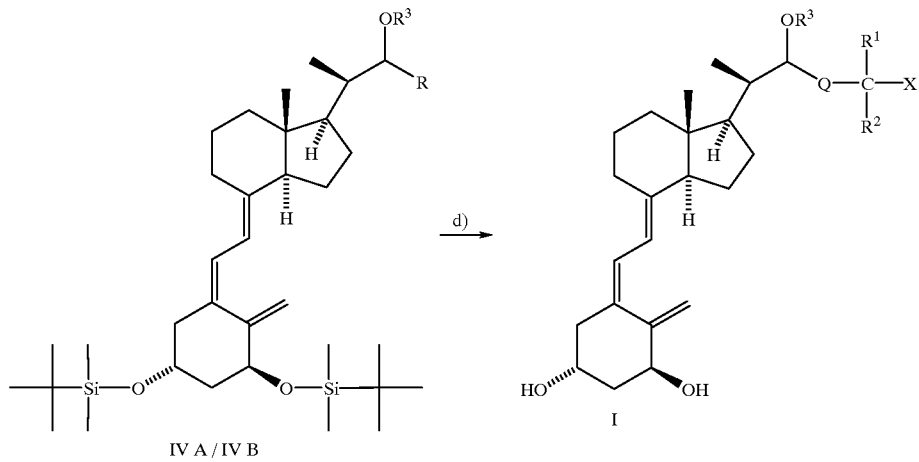

IV A / IV B $X^1$=H, OH, $OR^5$
$R^5$=alcohol protective group, e.g. tri(loweralkyl)-silyl or THP
$R^1$, $R^2$, $R^3$, Q and X have the above meanings.

Notes to Scheme 1
  a) (i) Compound 1 is reacted with an organometallic reagent R-Met-Hal or R-Met, such as e.g. RMgHal, where Hal is Cl, Br or I, or RLi, which may may be prepared from the side chain building block of general formula V, RHal, (see below) by reaction with a suitable metal, such as magnesium or lithium.
     (ii) The resulting mixture of the two C-22-epimers, IIA and IIB, is separated.
  b) Alkylation of the C-22-hydroxy compounds of type 11 to the corresponding compound III, where $R^3$=$C_1$–$C_{10}$ hydrocarbyl, or, optionally, acylation of the compounds of type II to the corresponding compound III, where $R^3$=$YR^4$; Y and $R^4$ having the above meanings.
  c) Isomerization of Compounds III to the corresponding compound IV, by means of UV-light in the presence of a triplet sensitizer, e.g. anthracene.
  d) Deprotection of Compounds IV to the corresponding compound I, e.g. by TBAF, by HF, or by TBAF followed by PPTS, or vice versa.

The compounds of type II or III may be subjected to optional functional group modification in the side chain, if considered desirable or necessary during a particular synthesis.

The order of the synthetic steps, which in Scheme 1 is: a), b), c), d), may, if for any reason desirable, be rearranged to the order: a), c), b), d), or the order: a), b), d), c).

The side chain building blocks of general formula V, RHal, are known compounds, or they can be prepared by standard methods known to the specialist.

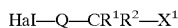

in which Hal, Q, $R^1$, $R^2$ and $X^1$ have the above meanings. In particular, this applies to the side chain building blocks of general formula V necessary for the preparation of the exemplified compounds (101–108, 110–112, 114–116 and 121); these RHal are described in table 2. Other similar RHal may be prepared by methods analogous to those used for synthesizing the compounds V of table 2. For $X^1$=O—THP, see e.g. WO 93/19044.

TABLE 2

Some Side Chain Building Blocks, R-Hal of General Formula V

| Compound | Formula | References |
|---|---|---|
| 501 | $Br(CH_2)_2C(CH_3)_2OSi(CH_3)_3$ | WO 91/00271 |
| 502 | $Br(CH_2)_2C(C_2H_5)_2OSi(CH_3)_3$ | WO 94/14766 |
| 503 | $Br(CH_2)_3C(CH_3)_3OSi(CH_3)_3$ | WO 91/15475 |
| 504 | $Br(CH_2)_3C(C_2H_5)_2OSi(CH_3)_3$ | WO 89/10351 |
| 505 | $Br(CH_2)_4C(C_2H_5)_2OSi(CH_3)_3$ | WO 89/10351 |

The reaction of the aldehyde 1 with the organometallic reagents derived from the side chain building blocks, e.g. RMgHal or RLi, can be performed by standard methods of nucleophilic addition of Grignard or lithium reagents to carbonyl compounds; i.e. by reacting the RHal with magnesium or lithium in a suitable anhydrous solvent, such as ether and/or THF, to generate the organometallic reagent, then adding 1, to give II after usual aqueous work-up (which is normally implied in all the reactions of Scheme 1. In general the reaction product II is a mixture of the two possible C-22-epimers, here designated IIA and IIB. It is usually preferable to separate the IIA and IIB epimers which can conveniently be done by chromatography.

Nonlimiting illustrations of such compounds of formula II are given in Table 3. In this table these compounds are described as separate 22-epimers IIA or IIB (preparations 1–5). The compounds IIA are formed in much higher yields than the corresponding IIB epimers, typically in the ratio of about 95 to 5.

The alkylation or acylation of the C-22-hydroxy compounds of general formula II to yield the corresponding compound III where $R^3$ is $C_1$–$C_3$ alkyl, aryl or aralkyl or $YR^4$ can be performed by standard methods well known to the specialist. Illustrative, but non limiting, compounds of this sort are listed in Table 3.

In the alkylation reaction use is preferably made of an alkylating agent $R^3Z$, in which Z stands for a good leaving group, such as for example Cl—, Br—, I—, $CH_3SO_3$—, p—$CH_3$—$C_6H_4$—$SO_3$— or $CF_3SO_3$—; the $R^3Z$ being allowed to react with the anion of the appropriate compound II or III ($R^3$=H), derived therefrom by means of a suitable strong base, such as an alkali-metal alkoxide, alkyl alkali-metal or alkali-metal hydride. A useful method is described in General Procedure 2, and in more detail in the included preparations; a suitable crown ether may be added as a phase transfer agent to accelerate the alkylation process.

In the acylation reaction producing compounds III where $R^3=YR^4$, use may advantageously be made of standard acylation procedures, such as reaction of the alcohol II with an acid chloride or acid anhydride ($R^4$ YCl or $(R^4Y)_2O$), or by forming the acylating agent in situ from the corresponding acid $R^4YOH$ and a dehydrating or condensing agent, such as e.g. a carbodiimide or an assisting acid anhydride, forming an intermediary mixed anhydride.

Furthermore, the addition of a suitable base, such as a tertiary amine, may often be profitably applied during the acylation; in many cases addition of a special heterocyclic amine like DMAP may accelerate the acylation process considerably. Examples of acylation procedures are given in General Procedure 3.

Table 3 also contains nonlimiting examples of photoisomerized compounds of general formula IV along with references to the preparation of each compound.

It should be noted that the preparations and examples of Tables 3 and 4 are illustrative only, the particular synthesis of each step and the order in which each step is performed can be varied greatly. Furthermore, the radical R: —Q—C$(R^1)(R^2)(X^1)$ may optionally be a radical which can be converted to this at any convenient later stage (or over several stages). Thus R in compounds II, III and IV does not necessarily have the same meaning along a particular synthetic sequence. The conversion of R to —Q—C$(R^1)(R^2)X^1$ may well involve several steps and possibly involve a temporary protection of the sensitive triene system of the molecule. Apart from any necessary modification of $R^3$ or within the side chain (R), the conversion of III to I involves a photoisomerisation step and a deprotection step, analogous to the steps used in the last stages of the synthesis of other vitamin D analogues (see European patent No. 0 227 836).

TABLE 3

Intermediates of General Formulas II, III & IV

| Type | Prep No. | Comp No. | Gen. Proc | \multicolumn{5}{c}{Radicals for formulas II, III & IV} |
|------|----------|----------|-----------|-------|-------|-------|-------|-------|
| 1)   | 2)       | 3)       | 4)        | $R^3$ | Q     | $R^1$ | $R^2$ | $XR^1$ |
| IIA  | 01 | 201 | 1  | —  | $(CH_2)_2$ | Me | Me | OTMS |
| IIA  | 02 | 202 | 1  | —  | $(CH_2)_2$ | Et | Et | OTMS |
| IIA  | 03 | 203 | 1  | —  | $(CH_3)_2$ | Me | Me | OTMS |
| IIA  | 04 | 204 | 1  | —  | $(CH_2)_3$ | Et | Et | OTMS |
| IIA  | 05 | 205 | 1  | —  | $(CH_2)_4$ | Et | Et | OTMS |
| IIIA | 06 | 301 | 2a | Me | $(CH_2)_2$ | Me | Me | OTMS |
| IIIA | 07 | 302 | 2a | Et | $(CH_2)_2$ | Me | Me | OTMS |
| IIIA | 08 | 303 | 2  | Me | $(CH_2)_2$ | Et | Et | OTMS |
| IIIA | 09 | 304 | 2  | Me | $(CH_2)_3$ | Me | Me | OTMS |
| IIIA | 10 | 305 | 2  | Me | $(CH_2)_3$ | Et | Et | OTMS |
| IIIA | 11 | 306 | 2a | Et | $(CH_2)_3$ | Et | Et | OTMS |
| IIIA | 12 | 307 | 2  | Me | $(CH_2)_4$ | Et | Et | OTMS |
| IIIA | 13 | 308 | 2a | Et | $(CH_2)_4$ | Et | Et | OTMS |
| IVA  | 14 | 401 | 4  | Me | $(CH_2)_2$ | Me | Me | OTMS |
| IVA  | 15 | 402 | 4  | Et | $(CH_2)_2$ | Me | Me | OTMS |
| IVA  | 16 | 403 | 4  | Me | $(CH_2)_2$ | Et | Et | OTMS |
| IVA  | 17 | 404 | 4  | Me | $(CH_2)_3$ | Me | Me | OTMS |
| IVA  | 18 | 405 | 4  | Me | $(CH_2)_3$ | Et | Et | OTMS |
| IVA  | 19 | 406 | 4  | Et | $(CH_2)_3$ | Et | Et | OTMS |
| IVA  | 20 | 407 | 4  | Me | $(CH_2)_4$ | Et | Et | OTMS |
| IVA  | 21 | 408 | 4  | Et | $(CH_2)_4$ | Et | Et | OTMS |

TABLE 3-continued

Intermediates of General Formulas II, III & IV

| Type | Prep No. | Comp No. | Gen. Proc | $R^3$ | Q | $R^1$ | $R^2$ | $XR^1$ |
|------|----------|----------|-----------|-------|---|-------|-------|--------|
| 1)   | 2)       | 3)       | 4)        |       |   |       |       |        |
| IIB  | 01 | 221 | 1  | —    | $(CH_2)_2$ | Me | Me | OTMS |
| IIIA | 22 | 310 | 2  | Et   | $(CH_2)_3$ | Me | Me | OTMS |
| IIIA | 23 | 311 | 2  | Me   | $(CH_2)_4$ | Me | Me | OTMS |
| IIIA | 24 | 312 | 2  | Et   | $(CH_2)_4$ | Me | Me | OTMS |
| IIIA | 25 | 314 | 2a | Pr   | $(CH_2)_2$ | Me | Me | OTMS |
| IIIA | 26 | 315 | 2  | Bn   | $(CH_2)_2$ | Me | Me | OTMS |
| IIIB | 34 | 321 | 2  | Me   | $(CH_2)_2$ | Me | Me | OTMS |
| IVA  | 27 | 410 | 4  | Et   | $(CH_2)_3$ | Me | Me | OTMS |
| IVA  | 28 | 411 | 4  | Me   | $(CH_2)_4$ | Me | Me | OTMS |
| IVA  | 29 | 412 | 4  | Et   | $(CH_2)_4$ | Me | Me | OTMS |
| IVA  | 30 | 414 | 4  | Pr   | $(CH_2)_2$ | Me | Me | OTMS |
| IVA  | 31 | 415 | 4  | Bn   | $(CH_2)_2$ | Me | Me | OTMS |
| IVA  | 32 | 416a* | 4 | H    | $(CH_2)_2$ | Me | Me | OTMS |
| IVA  | 33 | 416* | 3  | PhOCS | $(CH_2)_2$ | Me | Me | OTMS |
| IVB  | 35 | 421 | 4  | Me   | $(CH_2)_2$ | Me | Me | OTMS |

Notes to Table 3:
1) Type: See Scheme 1
2) Prep No. = Preparation Number
3) Comp No. = Compound Number
4) Gen. Proc = General Procedure Number
*Reversal of steps b) and c) of Scheme 1. Therefore, in compound 416a, $R^3$ stands for H Exemplified and planned Compounds I of the invention are listed in Table 4, the numbered examples giving reference to illustrative methods of synthesis, together with spectroscopic data for these exemplified compounds.

The planned Compounds, 109, 113, 117–120 and 122–135 are made in a sequence of synthetic steps which is analogous to the sequence used for the preparations of the exemplified Compounds, 101–108, 110–112, 114–116 and 121, Examples 1–15; see Scheme 1, and the notes to Scheme 1.

In the following, $R^4$, $R^5$, Hal, Z and Y have the above meanings, and Q, $R^1$, $R^2$ and $R^3$ have same meanings as they have in Table 4, for the corresponding planned compounds of formula 1. Compound 1 and the appropriate Compound V, Hal—Q—CR$^1$R$^2$—OR$^5$ (OR$^5$ being replaced by H in the case of the synthesis of Compound 131), are reacted, according to General Procedure 1 (GP 1), to give the corresponding compound of formula II.

The compound of formula II and the appropriate R$^3$Z are reacted, according to GP 2, to give the corresponding compound of formula III, except for the sequence leading to Compounds 134 and 135; in which cases the appropriate Compound II (Compound 201) is acylated, according to GP 3, with the appropriate acylating reagent R$^4$YCl or (R$^4$Y)$_2$O to give the corresponding compound of formula III.

The compound of formula III is photo-isomerized, according to GP 4, to give the corresponding compound of formula IV. As the last step, the compound of formula IV is deprotected, according to either GP 5, GP 6 or GP 7, to give the Compound I in question.

TABLE 4

Exemplified and Planned Compounds of General Formula I

| Exam No. 1) | Comp No. 2) | Isom C-22 3) | Gen. Proc 4) | $R^3$ | Q | $R^1$ | $R^2$ | X |
|---|---|---|---|---|---|---|---|---|
| 1 | 101 | A | 5 | Me | $(CH_2)_2$ | Me | Me | OH |
| 2 | 102 | A | 5 | Et | $(CH_2)_2$ | Me | Me | OH |
| 3 | 103 | A | 5 | Me | $(CH_2)_2$ | Et | Et | OH |
| 4 | 104 | A | 5 | Me | $(CH_2)_3$ | Me | Me | OH |
| 5 | 105 | A | 5 | Me | $(CH_2)_3$ | Et | Et | OH |
| 6 | 106 | A | 6 | Et | $(CH_2)_3$ | Et | Et | OH |
| 7 | 107 | A | 6 | Me | $(CH_2)_4$ | Et | Et | OH |
| 8 | 108 | A | 6 | Et | $(CH_2)_4$ | Et | Et | OH |
|  | 109 | A | 5–7 | Et | $(CH_2)_2$ | Et | Et | OH |
| 9 | 110 | A | 5 | Et | $(CH_2)_3$ | Me | Me | OH |
| 10 | 111 | A | 5 | Me | $(CH_2)_4$ | Me | Me | OH |
| 11 | 112 | A | 5 | Et | $(CH_2)_4$ | Me | Me | OH |
|  | 113 | A | 5–7 | Me | $CH_2$ | Me | Me | OH |
| 12 | 114 | A | 5 | Pr | $(CH_2)_2$ | Me | Me | OH |
| 13 | 115 | A | 5 | Bn | $(CH_2)_2$ | Me | Me | OH |
| 14 | 116 | A | 6 | PhOCS | $(CH_2)_2$ | Me | Me | OH |
|  | 117 | A | 5–7 | Me | $(CH_2)_2$ | $CF_3$ | $CF_3$ | OH |
|  | 118 | A | 5–7 | Et | $(CH_2)_2$ | $CF_3$ | $CF_3$ | OH |
|  | 119 | A | 5–7 | Me | $(CH_2)_2$ | $C_2F_5$ | $C_2F_5$ | OH |
|  | 120 | A | 5–7 | Et | $(CH_2)_2$ | $C_2F_5$ | $C_2F_5$ | OH |
| 15 | 121 | B | 5 | Me | $(CH_2)_2$ | Me | Me | OH |
|  | 122 | B | 5–7 | Et | $(CH_2)_2$ | Me | Me | OH |
|  | 123 | A | 5–7 | Me | $(CH_2)_3$ | $CF_3$ | $CF_3$ | OH |
|  | 124 | A | 5–7 | Et | $(CH_2)_3$ | $CF_3$ | $CF_3$ | OH |
|  | 125 | A | 5–7 | Me | $CH_2CF_2$ | Me | Me | OH |
|  | 126 | A | 5–7 | Et | $CH_2CF_2$ | Me | Me | OH |
|  | 127 | A | 5–7 | Me | $CH_2CF_2$ | $CF_3$ | $CF_3$ | OH |
|  | 128 | A | 5–7 | Et | $CH_2CF_2$ | $CF_3$ | $CF_3$ | OH |
|  | 129* | A | 5–7 | Me | $(CH_2)_2$ | Me | $CF_3$ | OH |
|  | 130# | A | 5–7 | Me | $(CH_2)_2$ | $CF_3$ | Me | OH |
|  | 131 | A | 5–7 | Me | $(CH_2)_2$ | Me | Me | H |
|  | 132 | A | 5–7 | Me | $(CH_2)_2$ | —$(CH_2)_4$— |  | OH |
|  | 133 | A | 5–7 | Me | $(CH_2)_2$ | —$(CH_2)_5$— |  | OH |
|  | 134 | A | 6 | PhSCO | $(CH_2)_2$ | Me | Me | OH |
|  | 135 | A | 6 | PhSCS | $(CH_2)_2$ | Me | Me | OH |

Notes to Table 4
1) Exam No. = Example Number
2) Comp No. = Compound Number
3) Isom C-22 = Isomer at carbon 22 of the side chain
4) Gen. Proc = General Procedure Number
*R-configuration of the carbon bearing $R^1$ and $R^2$
S-configuration of the carbon bearing $R^1$ and $R^2$ The present compounds are intended for use in pharmaceutical compositions which are useful in the local or systemic treatment of human and veterinary disorders as described above.

The present compounds may be used in combination with other pharmaceuticals or treatment modalities. In the treatment of psoriasis the present compounds may be used in combination with e.g. steroids or with other treatments e.g. light- or UV-light-treatment or the combined PUVA-treatment. In the treatment of cancer the present compounds may be used in combination with other anti-cancer drugs or anti-cancer treatments, such as radiation treatment. In the prevention of graft rejection and graft versus host reaction, or in the treatment of auto-immune diseases, the present compounds may advantageously be used in combination with other immunosuppressive/immunoregulating drugs or treatments, e.g. with cyclosporin A.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

While it is possible for an active ingredient to be administered alone as the raw chemical, it is preferable to present it as a pharmaceutical formulation. Conveniently, the active ingredient comprises from 0.1 ppm to 0.10% by weight of the formulation.

The formulations, both for veterinary and for human medical use, of the present invention thus comprise an active ingredient in association with a pharmaceutically acceptable carrier therefore and optionally other therapeutic ingredient (s). The carrier(s) must be "acceptable" in the sense of being compatible with the other ingredients of the formulations and not deleterious to the recipient thereof.

The formulations include e.g. those in a form suitable for oral, ophthalmic, rectal, parenteral (including subcutaneous, intramuscular and intravenous), transdermal, intra-articular and topical, nasal or buccal administration.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier, or in the form of an enema.

Formulations suitable for parenteral administration conveniently comprise a sterile oily or aqueous preparation of the active ingredient which is preferably isotonic with the blood of the recipient. Transdermal formulations may be in the form of a plaster.

Formulations suitable for intra-articular or ophthalmic administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Formulations suitable for administration to the nose or buccal cavity include powder, self-propelling and spray formulations, such as aerosols and atomizers.

In addition to the aforementioned ingredients, the formulations of this invention may include one or more additional ingredients, such as diluents, binders, preservatives etc.

The compositions may further contain other therapeutically active compounds usually applied in the treatment of the above mentioned pathological conditions, such as other immunosuppressants in the treatment of immunological diseases, or steroids in the treatment of dermatological diseases.

The present invention further concerns a method for treating patients suffering from one of the above pathological conditions, said method consisting of administering to a patient in need of treatment an effective amount of one or more compounds of formula 1, alone or in combination with one or more other therapeutically active compounds usually applied in the treatment of said pathological conditions. The treatment with the present compounds and/or with further therapeutically active compounds may be simultaneous or with intervals.

In the systemic treatment daily doses of from 0.001–2 µg per kilogram bodyweight, preferably from 0.002–0.3 µg/kg of mammal bodyweight, for example 0.003–0.3 pg/kg of a compound of formula I are administered, typically corresponding to a daily dose for an adult human of from 0.2 to 25 µg. In the topical treatment of dermatological disorders, ointments, creams or lotions containing from 0.1–500 µg/g, and preferably from 0.1–100 µg/g, of a compound of formula I are administered. For topical use in ophthalmology ointments, drops or gels containing from 0.1–500 pg/g, and preferably from 0.1–100 µg/g, of-a compound of formula I are administered. The oral compositions are formulated, preferably as tablets, capsules, or drops, containing from 0.05–50 µg, preferably from 0.1–25 µg, of a compound of formula 1, per dosage unit.

The invention will now be further described in the following General Procedures, Preparations and Examples:
General Procedures, Preparations and Examples General The exemplified compounds I are listed in Table 4.

For $^1$H NMR (300 MHz) and $^{13}$C NMR (75.6 MHz) spectra chemical shift values (δ) are quoted, unless otherwise specified, for deuteriochloroform solutions relative to internal tetramethylsilane (δ=0.00) or chloroform (δ=7.25 for 1H NMR) or deuteriochloroform (δ=76.81 for $^{13}$C NMR). The value for a multiplet, either defined (doublet (d), triplet (t), quartet (q)) or not (m) at the approximate mid point is given unless a range is quoted (s=singlet, b=broad).

Ether is diethyl ether, and was dried over sodium. THF was dried over sodium-benzophenone. Petroleum ether refers to the pentane fraction. Reactions were run at room temperature unless otherwise noted. The work-up procedure referred to involves dilution with the'specified solvent (otherwise the organic reaction solvent), extraction with water and then brine, drying over anhydrous $MgSO_4$, and concentration in vacuo to give a residue. Chromatography was performed on silica gel.

General Procedures

General Procedure 1: Reaction of Compound 1 with Grignard reagents, RMgHaI, derived from side chain building blocks V (RHaI). to give Compounds IIA and IIB (Scheme 1. Table 3) (Preparations 01–05)

To 0.12 g magnesium turnings (Grignard quality) in a dry flask was added, dropwise with stirring and in an argon atmosphere, a solution of the appropriate compound V (5.0 mmol) in a 1:1 mixture of dry THF and dry ether (6 ml). Stirring was continued under heating to reflux for 45 minutes. The resulting Grignard reagent was again cooled to 20° C., and a solution of the aldehyde, compound 1 (0.57 g; 1 mmole) in a 1:1 mixture of dry THF and dry ether (2 ml) was added dropwise, during 5 minutes, followed by stirring at 20° C. for 30 minutes. The reaction mixture was poured into a 10% aqueous solution of ammonium chloride and worked up (ether) to yield a crude product containing compounds IIA and IIB which were separated and purified by chromatography (mixture of ether and pet.ether as eluant) to yield the title compounds of the preparation. (If necessary, repeated chromatography of selected fractions were performed, possibly using mixtures of pet.ether, dichlormethane and ethylacetate, e.g. a 80:20:2 mixture, as eluant. Conveniently the purification/separation may take place in the form of PLC or using a preparative HPLC apparatus).

General Procedure 2: Alkylation of C-22-hydroxy-compounds of type II or III to the corresponding compound III where $R^3=C_1-C_{10}$ hydrocarbyl (Scheme 1, Table 3) (Preparations 06–13 and 22–23)

To a solution of the appropriate compound II or III (0.25 mmol) in dry THF (4 ml) was added, while stirring at 20° C. under argon, a 20% suspension of potassium hydride in mineral oil (0.1 ml) followed by an alkylating agent, $R^3Z$ (0.75 mmol), and the mixture was stirred for 5 minutes, after which 18-Crown-6 (0.07 g) was added. Stirring at 20° C. was continued for 1.5 hours, after which the reaction mixture was worked up (ether). The crude product was purified by chromatography (mixture of ether and pet.ether as eluant) to yield the title compound of the preparation.

Variation: General Procedure 2a

The procedure of General Procedure 2 was followed, except that after stirring of the reaction mixture for 1.5 hours as described, another portion of potassium hydride (20% in mineral oil) (0.1 ml), of alkylating agent $R^3Z$ (0.75 mmol), and of 18-crown-6 (0.07 g) was added, and the mixture was stirred for another 1.5 hours.

General Procedure 3: Acylation of C-22-hydroxy-compounds of type II or III to the corresponding compound III where $R^3=YR^4$ (Scheme 1 Table 3) (Preparation 33)

To a solution of the appropriate compound II or III (0.25 mmol) in a suitable dry solvent, e.g. dichloromethane, was added, while stirring at 20° C. under argon, an acylating reagent ($R^4YCl$, $(R^4Y)_2O$ or $R^4YOH$), preferably accompanied by one or two suitable bases, such as triethylamine, pyridine and/or DMAP. In the case where an acid, $R^4YOH$, was used, the addition of a dehydrating or condensing agent such as e.g. dicyclohexyl carbodiimide was desirable. The reaction mixture was then stirred at a suitable temperature (from room temperature up to the boiling point of the solvent) for a sufficient time (typically for 1 to 4 hours).

After a suitable work-up the crude product was purified by chromatography to yield the title compound of the preparation.

General Procedure 4: Isomerization of Compounds III to the corresponding compound IV (Scheme 1, Table 3) (Preparations 14–21 and 27–35)

A solution of the appropriate compound III (0.3 mmol), anthracene (120 mg) and triethylamine (0.05 ml) in dichloromethane (20 ml) under argon in a Pyrex flask was irradiated with UV-light from a high pressure ultraviolet lamp, type TQ760Z2 (Hanau) at about 1I0° C. for 20 minutes under stirring. The reaction mixture was concentrated in vacuo and treated with pet.ether (2×5 ml). After filtering the filtrate was concentrated in vacuo and purified by chromatography (mixture of ether and pet.ether as eluant) to yield the title compound of the preparation. General Procedure 5: Deprotection of Compounds IV to the corresponding Compounds I by treatment with tetra-n-butyl-ammoniumfluoride (Scheme 1. Table 4) (Examples 1–5, 9–11, 12–13 and 15)

To a solution of the appropriate compound IV (0.16 mmol) in THF (5 ml) was added a solution of tetra-n-butylammonium fluoride (300 mg) in THF (5 ml) while stirring at 60° C. under argon. Stirring was continued for one hour at 60° C., and the reaction mixture was worked up (ethyl acetate with an additional extraction with aqueous sodium hydrogen carbonate). The residue after evaporation was purified by chromatography (50% to 0% pet.ether in ethyl acetate as eluant) to yield the title compound of the example.

General Procedure 6: Deprotection of Compounds IV to the corresponding Compound I by treatment with HF (Scheme 1, Table 4) (Examples 6–8 and 14)

To a solution of the appropriate compound IV (0.07 mmol) in ethyl acetate (0.2 ml) was added acetonitrile (2 ml) followed by a 5% solution of hydrofluoric acid in acetonitrile:water, 7:1 (1.2 ml) under argon and with stirring. Stirring was continued for 45 minutes at 20° C. Saturated aqueous sodium bicarbonate solution (10 ml) was added, and the reaction mixture was worked up (ethyl acetate) The residue was purified by chromatography (50% to 0% pet.ether in ethyl acetate as eluant) to yield the title compound of the example.

General Procedure 7: Deprotection of compounds IV to the correspondding Compounds I by treatment with tetra-n-butylammoniumfluoride followed by pyridine-p-toluenesulfonate[2] (Scheme 1, Table 4)

[2] or in the reverse order

To a solution of the appropriate compound IV (0.16 mmol) in THF (5 ml) was added a solution of tetra-n-butylammonium fluoride (300 mg) in THF (5 ml) while stirring at 60° C. under argon. Stirring was continued for one hour at 60° C., and the reaction mixture was worked up (ethyl acetate with an additional extraction with aqueous sodium hydrogen carbonate). The residue after evaporation was purified by chromatography (50% to 0% pet.ether in ethyl acetate as eluant) and then dissolved in absolute ethyl alcohol (2 ml). PPTS (2 mg) was added, and the mixture was stirred for one hour at 50° C. under argon. After work-up (ethyl acetate with an additional aqueous sodium bicarbonate extraction) the residual crude product was purified by chromatography (50% to 0% pet.ether in ethyl acetate as eluant) to yield the title compound of the example.

Preparations

Preparation 01: Compounds 201 and 221
Method: General Procedure 1.
Starting material V: Compound 501
Chromatography eluant: 0% to 5% ether in pet.ether.
$^1$H NMR for 201: δ=0.06 (m, 12H), 0.11 (s, 9H), 0.54 (s, 3H), 0.85 (d, 3H), 0.86 (s, 9H), 0.89 (s, 9H), 1.23 (s, 6H), 1.20–2.15 (m, 19H), 2.31 (bd, 1H), 2.55 (dd, 1H), 2.88 (m, 1H), 380 (m, 1H), 4.21 (m, 1H), 4.52 (m, 1H), 4.94 (m, 1H), 4.98 (m, 1H), 5.82 (d, 1H), 6.45 (d, 1H).
$^{13}$C NMR for 221: 153.4, 142.8, 135.3, 121.5, 116.3, 106.5, 74.1, 73.8, 70.1, 67.0, 56.1, 52.7, 45.7, 43.8, 41.8, 41.2, 39.8, 36.4, 29.9, 29.5, 28.7, 26.7, 25.7, 25.6, 25.2, 23.3, 21.9, 18.1, 17.9, 12.4, 12.2, 2.3, −5.0, −5.1,-

Preparation 02: Compound 202
Method: General Procedure 1.
Starting material V: Compound 502
Chromatography eluant: 5% ether in pet.ether.
$^1$H NMR: δ=0.05 (m, 12H), 0.11 (s, 9H), 0.54 (s, 3H), 0.82 (t, 6H), 0.83 (d, 3H), 0.86 (s, 9H), 0.89 (s, 9H), 1.15–2.15 (m, 23H), 2.31 (m, 1H), 2.55 (dd, 1H), 2.88 (m, 1H), 3.77 (m, 1H), 4.21 (m, 1H), 4.52 (m, 1H), 4.93 (m, 1H), 4.98 (m, 1H), 5.82 (d, 1H), 6.45 (d. 1H).

Preparation 03: Compound 203
Method: General Procedure 1.
Starting material V: Compound 503
Chromatography eluant: 5% ether in pet.ether.
$^1$H NMR: δ32 0.06 (m, 12H), 0.10 (s, 9H), 0.55 (s, 3H), 0.83 (d, 3H), 0.86 (s, 9H), 0.89 (s, 9H), 1.20 (s, 6H), 1.15–2.15 (m, 21H), 2.31 (bd, 1H), 2.55 (dd, 1H), 2.88 (m, 1H), 3.85 (m, 1H), 4.21 (m, 1H), 4.52 (m, 1H), 4.94 (m, 1H), 4.98 (m, 1H), 5.83 (d, 1H), 6.45 (d, 1H).

Preparation 04: Compound 204
Method: General Procedure 1.
Starting material V: Compound 504
Chromatography eluant: 10% ether in pet.ether.
$^1$H NMR: δ=0.06 (m, 12H), 0.09 (s, 9H), 0.55 (s, 3H), 0.81 (t, 6H), 0.83 (d, 3H), 0.86 (s, 9H), 0.89 (s, 9H), 1.45 (q, 4H), 1.15–2.15 (m, 21H), 2.31 (bd, 1H), 2.55 (dd, 1H), 2.88 (m, 1H), 3.85 (m, 1H), 4.22 (m, 1H), 4.53 (m, 1H), 4.94 (m, 1H), 4.98 (m, 1H), 5.83 (d, 1H), 6.45 (d, 1H).

Preparation 05: Compound 205
Method: General Procedure 1.
Starting material V: Compound 505
Chromatography eluant: 0% to 5% ether in pet.ether.
$^1$H NMR: δ=0.05 (m, 12H), 0.08 (s, 9H), 0.54 (s, 3H), 0.79 (t, 6H), 0.83 (d, 3H), 0.85 (s, 9H), 0.89 (s, 9H), 1.10–2.10 (m, 27H), 2.31 (bd, 1H), 2.55 (dd, 1H), 2.88 (m, 1H), 3.84 (m, 1H), 4.21 (m, 1H), 4.53 (m, 1H), 4.94 (m, 1H), 4.98 (m, 1H), 5.82 (d, 1H), 6.45 (d, 1H).

Preparation 06: Compound 301
Method: General Procedure 2a.
Alkylating agent $R^3Z$: Methyl iodide
Starting material II: Compound 201
Chromatography eluant: 0% to 20% ether in pet.ether.
$^1$H NMR: δ=0.06 (m, 12H), 0.10 (s, 9H), 0.51 (s, 3H), 0.83 (d, 3H), 0.86 (s, 9H), 0.89 (s, 9H), 1.20 (s, 3H), 1.21 (s, 3H), 1.25–2.10 (m, 18H), 2.31 (bd, 1H), 2.55 (dd, 1H), 2.88 (m, 1H), 3.18 (m, 1H), 3.33 (s, 3H), 4.21 (m, 1H), 4.52 (m, 1H), 4.94 (m, 1H), 4.98 (m, 1H), 5.82 (d, 1H), 6.45 (d, 1H).

Preparation 07: Compound 302
Method: General Procedure 2a.

Starting material II: Compound 201
Alkylating agent R³Z: Ethyl iodide
Chromatography eluant: 0% to 3% ether in pet.ether.
¹H NMR: δ=0.05 (m, 12H), 0.09 (s, 9H), 0.50 (s, 3H), 0.84 (d, 3H), 0.86 (s, 9H), 0.89 (s, 9H), 1.17 (t, 3H), 1.20 (s, 3H), 1.21 (s, 3H), 1.10–2.10 (m, 18H), 2.31 (bd, 1H), 2.55 (dd, 1H), 2.88 (m, 1H), 3.20 (m, 1H), 3.47 (m, 2H), 4.22 (m, 1H), 4.52 (m, 1H), 4.93 (m, 1H), 4.98 (m, 1H), 5.81 (d, 1H), 6.45 (d, 1H).

Preparation 08: Compound 303
Method: General Procedure 2.
Starting material II: Compound 202
Alkylating agent R³Z: Methyl iodide
Chromatography eluant: 0% to 20% ether in pet.ether.
¹H NMR: δ=0.06 (m, 12H), 0.10 (s, 9H), 0.52 (s, 3H), 0.82 (t, 6H), 0.83 (d, 3H), 0.86 (s, 9H), 0.89 (s, 9H), 1.20–2.15 (m, 22H), 2.31 (bd, 1H), 2.55 (dd, 1H), 2.88 (m, 1H), 3.18 (m, 1H), 3.33 (s, 3H), 4.21 (m, 1H), 4.53 (m, 1H), 4.93 (m, 1H), 4.98 (m, 1H), 5.82 (d, 1H), 6.46 (d, 1H).

Preparation 09: Compound 304
Method: General Procedure 2.
Starting material II: Compound 203
Alkylating agent R³Z: Methyl iodide
Chromatography eluant: 0% to 2% ether in pet.ether.
¹H NMR: δ=0.06 (m, 12H), 0.09 (s, 9H), 0.52 (s, 3H), 0.83 (d, 3H), 0.86 (s, 9H), 0.89 (s, 9H), 1.19 (s, 3H), 1.20 (s, 3H), 1.10–2.15 (m, 20H), 2.31 (bd, 1H), 2.55 (dd, 1H), 2.88 (m, 1 (H), 3.22 (m, 1.H), 3.33 (s, 3 (H), 4.21 (m, 1H), 4.52 (m, 1H), 4.93 (m, 1H), 4.98 (m, 1H), 5.82 (d, 1H), 6.45 (d, 1H).

Preparation 10: Compound 305
Method: General Procedure 2.
Starting material II: Compound 204
Alkylating agent R³Z: Methyl iodide
Chromatography eluant: 0% to 20% ether in pet.ether.
¹H NMR: δ=0.06 (m, 12H), 0.10 (s, 9H), 0.52 (s, 3H), 0.81 (t, 6H), 0.83 (d, 3H), 0.86 (s, 9H), 0.89 (s, 9H), 1.15–2.10 (m, 24H), 2.31 (bd, 1H), 2.55 (dd, 1H), 2.88 (m, 1H), 3.21 (m, 1H), 3.33 (s, 3H), 4.21 (m, 1H), 4.52 30 (m, 1H), 4.93 (m, 1H), 4.98 (m, 1H), 5.82 (d, 1H), 6.45 (d, 1H).

Preparation II: Compound 306
Method: General Procedure 2a.
Starting material II: Compound 204
Alkylating agent R³Z: Ethyl bromide
Chromatography eluant: 0% to 20% ether in pet.ether.
¹H NMR: δ=0.06 (m, 12H), 0.08 (s, 9H), 0.50 (s, 3H), 0.81 (t, 6H), 0.83 (d, 3H), 0.86 (s, 9H), 0.89 (s, 9H), 1.17 (t, 3H), 1.10–2.10 (m, 24H), 2.31 (bd, 1H), 2.55 (dd, 1H), 2.88 (m, 1H), 3.24 (m, 1H), 3.47 (m, 2H), 4.21 (m, 1H), 4.53 (m, 1H), 4.93 (m, 1H), 4.98 (m, 1H), 5.82 (d, 1H), 6.45 (d, 1H).

Preparation 12: Compound 307
Method: General Procedure 2.
Starting material II: Compound 205
Alkylating agent R³Z: Methyl iodide Chromatography eluant: 0% to 20% ether in pet.ether.
¹ H NMR: δ=0.06 (m, 12H), 0.09 (s, 9H), 0.51 (s, 3H), 0.80 (t, 6H), 0.83 (d, 3H), 0.86 (s, 9H), 0.89 (s, 9H), 1.44 (q 4H), 1.15–2.10 (m, 22H), 2.31 (bd, 1H), 2.55 (dd, 1H), 2.88 (m, 1H), 3.22 (m, 1H), 3.33 (s, 3H), 4.21 (m, 1H), 4.53 (m, 1H), 4.93 (m, 1H), 4.98 (m, 1H), 5.82 (d, 1H), 6.45 (d, 1H).

Preparation 13: Compound 308
Method: General Procedure 2a.
Starting material II: Compound 205
Alkylating agent R³Z: Ethyl bromide
Chromatography eluant: 0% to 20% ether in pet.ether.
¹H NMR: δ=0.05 (m, 12H), 0.09-(s, 9H), 0.50 (s, 3H), 0.80 (t, 6H), 0.83 (d, 3H), 0.86 (s, 9H), 0.89 (s, 9H), 1.17 (t, 3H), 1.44 (q, 4H), 1.15–2.10 (m, 22H), 2.31 (bd, 1H), 2.55 (dd, 1H), 2.88 (m, 1H), 3.22 (m, 1H), 3.47 (m, 2H), 4.21 (m, 1H), 4.53 (m, 1H), 4.93 (m, 1H), 4.98 (m, 1H), 5.82 (d, 1H), 6.45 (d, 1H).

Preparation 14: Compound 401
Method: General Procedure 4.
Starting material III: Compound 301
Chromatography eluant: 5% ether in pet.ether.
¹H NMR: δ=0.06 (m, 12H), 0.11 (s, 9H), 0.50 (s, 3H), 0.82 (d, 3H), 0.87 (s, 18H), 1.20 (s, 3H), 1.21 (s, 3H), 1.15–2.10 (m, 18H), 2.21 (dd, 1H), 2.44 (dd, 1H), 2.82 (m, 1H), 3.18 (m, 1H), 3.32 (s, 3H), 4.18 (m, 1H), 4.37 (m, 1H), 4.86 (m, 1H), 5.17 (m, 1H), 6.01 (d, 1H), 6.23 (d, 1H).

Preparation 15: Compound 402
Method: General Procedure 4.
Starting material III: Compound 302
Chromatography eluant: 2.5% ether in pet.ether.
¹H NMR: δ=0.06 (m, 12H), 0.10 (s, 9H), 0.49 (s, 3H), 0.83 (d, 3H), 0.88 (s, 18H), 1.17 (t, 3H), 1.20 (s, 3H), 1.21 (s, 3H), 1.10–2.10 (m, 18H), 2.21 (dd, 1H), 2.44 (dd, 1H), 2.83 (m, 1H), 3.20 (m, 1H), 3.47 (m, 2H), 4.18 (m, 1H), 4.37 (m, 1H), 4.86 (m, 1H), 5.17 (m, 1H), 6.01 (d, 1H), 6.23 (d, 1H).

Preparation 16: Compound 403
Method: General Procedure 4.
Starting material III: Compound 303
Chromatography eluant: 0% to 2% ether in pet.ether.
¹H NMR: δ=0.06 (m, 12H), 0.10 (s, 9H), 0.50 (s, 3H), 0.82 (m, 9H), 0.87 (s, 9H), 0.88 (s, 9H), 1.20–2.10 (m, 22H), 2.21 (dd, 1H), 2.44 (dd, 1H), 2.82 (m, 1H), 3.18 (m, 1H), 3.32 (s, 3H), 4.18 (m, 1H), 4.38 (m, 1H), 4.86 (m, 1H), 5.18 (m, 1H), 6.01 (d, 1H), 6.23 (d, 1H).

Preparation 17: Compound 404
Method: General Procedure 4.
Starting material III: Compound 304
Chromatography eluant: 2% ether in pet.ether.
¹H NMR: δ=0.05 (m, 12H), 0.09 (s, 9H), 0.50 (s, 3H), 0.81 (d, 3H), 0.86 (s, 18H), 1.19 (s, 3H), 1.20 (s, 3H), 1.15–2.07 (m, 20H), 2.21 (dd, 1H), 2.44 (dd, 1H), 2.82 (m, 1H), 3.22 (m, 1H), 3.32 (s, 3H), 4.18 (m, 1H), 4.37 (m, 1H), 4.86 (m, 1H), 5.17 (m, 1H), 6.00 (d, 1H), 6.23 (d, 1H).

Preparation 18: Compound 405
Method: General Procedure 4.
Starting material III: Compound 305
Chromatography eluant: 0% to 3% ether in pet.ether.
¹H NMR: δ=0.06 (m, 12H), 0.09 (s, 9H), 0.51 (s, 3H), 0.81 (m, 9H), 0.88 (s, 18H), 1.15–2.10 (m, 24H), 2.21 (dd, 1H), 2.43 (dd, 1H), 2.82 (m, 1H), 3.21 (m, 1H), 3.32 (s, 3H), 4.18 (m, 1H), 3.37 (m, 1H), 4.86 (m, 1H), 5.17 (m, 1H), 6.01 (d, 1H), 6.23 (d, 1H).

Preparation 19: Compound 406
Method: General Procedure 4.
Starting material III: Compound 306
Chromatography eluant: 0% to 2% ether in pet.ether.

¹H NMR: δ=0.06 (m, 12H), 0.08 (s, 9H), 0.49 (s, 3H), 0.81 (t, 6H), 0.82 (d, 3H), 0.87 (s, 18H), 1.17 (t, 3H), 1.10–2.10 (m, 24H), 2.21 (dd, 1H), 2.44 (dd, 1H), 2.82 (m, 1H), 3.23 (m, 1H), 3.47 (q, 2H), 4.18 (m, 1H), 4.37 (m, 1H), 4.86 (m, 1H), 5.18 (m, 1H), 6.01 (d, 1H), 6.23 (d, 1H).

Preparation 20: Compound 407
Method: General Procedure 4.
Starting material III: Compound 307
Chromatography eluant: 0% to 2% ether in pet.ether.
¹H NMR: δ=0.06 (m, 12H), 0.09 (s, 9H), 0.50 (s, 3H), 0.80 (t, 6H), 0.81 (d, 3H), 0.87 (s, 18H), 1.44 (q, 4H), 1.10–2.10 (m, 22H), 2.21 (dd, 1H), 2.44 (dd, 1H), 2.83 (m, 1H), 3.21 (m, 1H), 3.32 (s, 3H), 4.18 (m, 1H), 4.36 (m, 1H), 4.86 (m, 1H), 5.17 (m, 1H), 6.01 (d, 1H), 6.23 (d, 1H).

Preparation 21: Compound 408
Method: General Procedure 4.
Starting material III: Compound 308
Chromatography eluant: 0% to 2% ether in pet.ether.
¹H NMR: δ 0.06 (m, 12H), 0.09 (s, 9H), 0.49 (s, 3H), 0.79 (t, 6H), 0.80 (d, 3H), 0.87 (s, 18H), 1.17 (t, 3H), 1.44 (q, 4H), 1.07–2.10 (m, 22H), 2.21 (dd, 1H), 2.44 (dd, 1H), 2.83 (m, 1H), 3.22 (m, 1H), 3.47 (m, 2H), 4.18 (m, 1H), 4.36 (m, 1H), 4.86 (m, 1H), 5.17 (m, ₁H), 6.01 (d, 1H), 6.23 (d, 1H).

Preparation 22: Compound 310
Method: General Procedure 2.
Starting material II: Compound 203
Alkylating agent R³Z: Ethyl bromide
Chromatography eluant: 0% to 5% ether in pet.ether.
¹³C NMR: 153.4, 143.3, 135.1, 121.6, 116.1, 106.4, 82.6, 73.8, 70.1, 67.0, 64.2, 55.6, 50.7, 46.1, 44.9, 43.8, 39.2, 36.4, 35.0, 31.1, 29.7, 29.6, 28.9, 25.7, 25.6, 25.0, 23.2, 22.1, 21.1, 18.1, 17.9, 15.6, 12.8, 12.7, 2.4, −4.9, −5.0, −5.1, −5.1.

Preparation 23: Compound 311
Method: General Procedure 2.
Starting material II: Compound 114j of WO91/00271
Alkylating agent R³Z: Methyl iodide
Chromatography eluant: 0% to 20% ether in pet.ether.
¹³C NMR: 153.4, 143.2, 135.1, 121.6, 116.2, 106.4, 83.4, 73.8, 70.1, 67.0, 56.4, 55.8, 51.2, 45.9, 44.8, 43.8, 39.6, 36.4, 35.4, 30.2, 29.7, 29.6, 28.8, 26.7, 25.8, 25.7, 25.6, 24.5, 23.3, 22.0, 18.1, 17.9, 12.6, 12.3, 2.4, −4.9, −5.0, −5.1, −5.1

Preparation 24: Compound 312
Method: General Procedure 2.
Starting material II:Compound 114j of WO91/00271
Alkylating agent R³Z: Ethyl bromide
Chromatography eluant: 0% to 20% ether in pet.ether.
¹³C NMR: 153.4, 143.3, 135.1, 121.6, 116.1, 106.4, 82.5, 73.8, 70.1, 67.0, 64.2, 55.7, 50.8, 46.1, 44.8, 43.8, 39.2, 36.4, 35.1, 30.8, 29.7, 29.6, 28.9, 26.9, 25.7, 25.6, 25.1, 24.5, 23.3, 22.1, 18.1, 17.9, 15.6, 12.8, 12.6, 2.4, 4.9, −5.0, −5.1, −5.1

Preparation 25: compound 314
Method: General Procedure 2a.
Starting material II: Compound 201
Alkylating agent R³Z: n-Propyl bromide
Chromatography eluant: 0% to 5% ether in pet.ether.
¹³C NMR: 153.5, 143.3, 135.1, 121.6, 116.1, 106.4, 83.0, 73.8, 70.6, 70.1, 67.0, 55.7, 50.9, 46.1, 43.8, 41.2, 39.4, 36.4, 35.3, 29.8, 29.6, 28.9, 25.7, 25.6, 25.3, 25.2, 23.4, 23.3, 22.1, 18.1, 17.9, 12.6, 10.7, 2.4, 4.9, −5.0, −5.1, −5.1

Preparation 26: Compound 315
Method: General Procedure 2.

Starting material II: Compound 201
Alkylating agent R³Z: Benzyl bromide
Chromatography eluant: 0% to 5% ether in pet.ether.
¹³C NMR: 153.4, 143.2, 138.1, 135.1, 128.0, 127.4, 127.0, 121.6, 116.2, 106.4, 82.7, 73.7, 70.4, 70.1, 67.0, 55.7, 51.1, 46.0, 43.8, 41.2, 39.5, 36.4, 35.5, 29.8, 29.6, 28.8, 25.7, 25.6, 25.5, 25.2, 23.2, 22.0, 18.1, 17.9, 12.6, 12.5, 2.4, −4.9, −5.0, −5.1, −5.1

Preparation 27: Compound 410
Method: General Procedure 4.
Starting material III: Compound 310
Chromatography eluant: 0% to 5% ether in pet.ether.
¹³C NMR: 148.1, 140.9, 134.7, 123.0, 117.6, 111.0, 82.7, 73.8, 71.8, 67.3, 64.2, 55.5, 50.7, 46.0, 45.8, 44.9, 44.6, 39.2, 35.0, 31.2, 29.7, 29.6, 28.8, 25.7, 25.6, 25.0, 23.2, 22.0, 21.1, 18.1, 18.0, 15.6, 12.9, 12.6, 2.4, 4.9, −5.0, −5.3

Preparation 28: Compound 411
Method: General Procedure 4.
Starting material III: Compound 311
Chromatography eluant: 0% to 5% ether in pet.ether.
¹³C NMR: 148.1, 140.8, 134.8, 123.0, 117.6, 111.0, 83.4, 73.7, 71.8, 67.3, 56.4, 55.6, 51.2, 45.8, 45.7, 44.7, 44.6, 39.7, 35.4, 30.1, 29.7, 29.6, 28.7, 26.7, 25.8, 25.7, 25.6, 24.5, 23.3, 21.9, 18.0, 17.9, 12.5, 12.3, 2.4, −4.9, −5.0, −5.3

Preparation 29: Compound 412
Method: General Procedure 4.
Starting material III: Compound 312
Chromatography eluant: 0% to 5% ether in pet.ether.
¹³C NMR: 148.1, 140.9, 134.7, 123.0, 117.6, 111.0, 82.6, 73.8, 71.8, 67.3, 64.2, 55.5, 50.7, 46.0, 45.8, 44.8, 44.6, 39.3, 35.1, 30.8, 29.7, 29.6, 28.8, 26.9, 25.7, 25.7, 25.6, 25.1, 24.5, 23.2, 22.0, 18.1, 15.6, 12.8, 12.6, 2.4, −4.9, −5.0, −5.3

Preparation 30: Compound 414
Method: General Procedure 4.
Starting material III: Compound 314
Chromatography eluant: 0% to 1% ether in pet.ether.
¹³C NMR: 148.1, 140.9, 134.7, 123.0, 117.6, 111.0, 83.0, 73.8, 71.8, 70.6, 67.3, 55.6, 50.9, 45.9, 45.8, 44.6, 41.2, 41.2, 39.5, 35.3, 29.8, 29.6, 27.5, 25.7, 25.6, 25.3, 25.2, 23.4, 22.4, 20.2, 19.2, 14.1, 12.6, 10.7, 2.4, −4.9, −5.0, −5.3

Preparation 31: Compound 415
Method: General Procedure 4.
Starting material III: Compound 315
Chromatography eluant: 001 to 1% ether in pet.ether.
¹³C NMR: 148.1, 140.8, 139.3, 134.8, 128.0, 127.2, 127.0, 123.0, 117.6, 111.0, 82.7, 73.7, 71.8, 70.4, 67.3, 55.6, 51.1, 45.9, 45.8, 44.6, 41.2, 39.5, 35.5, 29.8, 29.6, 28.7, 25.7, 25.6, 25.5, 25.2, 23.2, 21.9, 18.1, 18.0, 12.6, 12.5, 2.4, −4.8, −4.9, −5.0, −5.3

Preparation 32: Compound 416a
Method: General Procedure 4.
Starting material II: Compound 201
Chromatography eluant: 0% to 10% ether in pet.ether.
¹³C NMR: 148.1, 140.6, 134.9, 122.9, 117.8, 111.0, 73.9, 73.0, 71.9, 67.3, 56.0, 52.3, 45.8, 45.3, 44.6, 41.6, 40.0, 39.8, 29.8, 29.7, 29.6, 28.7, 27.2, 25.7, 25.6, 23.2, 21.8, 18.0, 17.9, 12.2, 11.2, 2.4, −4.9, −5.0, −5.3

Preparation 33: Compound 416
Method: General Procedure 3.
Starting material IV: Compound 416a
Acylating reagent: Phenyl chlorothionoformate (125 mg)

Bases: Pyridine (0.2 ml); 4-Dimethylaminopyridine (115 mg)

Solvent: Dichloromethane (4 ml).

Reaction temperature: 20° C.

Reaction time: 7 hours.

Chromatography eluant: 5% ether in pet.ether.

$^{13}$C NMR: 194.3, 153.1, 148.2, 140.4, 135.0, 129.2, 126.2, 122.9, 121.9, 117.8, 111.0, 89.2, 73.3, 71.8, 67.3, 55.5, 51.3, 45.8, 45.6, 44.6, 40.2, 39.1, 34.9, 29.9, 29.4, 28.7, 25.7, 25.6, 25.4, 24.3, 23.1, 21.9, 18.1, 18.0, 12.6, 12.4, 2.4, −4.9, −5.0, −5.3

Preparation 34: Compound 321

Method: General Procedure 2.

Alkylating agent R$^3$ Z: Methyl iodide

Starting material II: Compound 221

Reaction time: 15 minutes

Chromatography eluant: 15% ether in pet.ether: PLC.

$^1$H NMR: δ=6.45 (d, 1H), 5.83 (d, 1H), 4.98 (m, 1H), 4.93 (m, 1H), 4.53 (m, 1H), 4.22 (m, 1H), 3.30 (s, 3H), 3.24 (m, 1H), 2.88 (m, 1H), 2.55 (dd, 1H), 2.31 (m, 1H), 2.08–1.15 (m, 18H), 1.22 (s, 3H), 1.19 (s, 3H), 0.89 (s, 9H), 0.86 (s, 9H), 0.81 (d, 3H), 0.58 (s, 3H), 0.10 (s, 9H), 0.05 (m, 12H)

Preparation 35: Compound 421

Method: General Procedure 4.

Starting material III: Compound 321

Chromatography eluant: 0% to 1% ether in pet.ether.

$^1$H NMR: δ=6.24 (d, 1H), 6.03 (d, 1H), 5.18 (m, 1H), 4.87 (m, 1H), 4.37 (m, 1H), 4.19 (m, 1H), 3.31 (s, 3H), 3.24 (m, 1H), 2.83 (m, 1H), 2.45 (dd, 1H), 2.22 (dd, 1H), 2.07–1.00 (m, 1 8H), 1.23 (s, 3H), 1.20 (s, 3H), 0.88 (s, 18H), 0.83 (d, 3H), 0.58 (s, 3H), 0.11 (s, 9H), 0.06 (m, 12H)

EXAMPLES

Example 1

1(S),3(R)-Dihydroxy-20(R)-(1-methoxy-4-hydroxy-4-methyl-1-pentyl)-9,10-seco-pregna-5(Z),7(E)10 (19)-triene; isomer A (Compound 101)

Method: General Procedure 5.

Starting material IV: Compound 401.

Chromatography eluant: 50% to 0% pet.ether in ethylacetate.

$^1$H NMR: δ=0.52 (s, 3H), 0.84 (d, 3H), 1.22 (s, 3H), 1.23 (s, 3H), 1.15–2.10 (m, 21H), 2.31 (dd, 1H), 2.59 (dd, 1H), 2.84 (m, 1H), 3.17 (m, 1H), 3.34 (s, 3H), 4.22 (m, 1H), 4.42 (m, 1H), 5.00 (m, 1H), 5.33 (m, 1H), 6.02 (d, 1H), 6.37 (d, 1H).

Example 2

1(S),3(R)-Dihydroxy-20(R)-(1-ethoxy-4-hydroxy-4-methyl-1-pentyl)-9,10-seco-pregna-5(Z),7(E),-10 (19)-triene: isomer A (Compound 102)

Method: General Procedure 5.

Starting material IV: Compound 402.

Chromatography eluant: 50% to 0% pet.ether in ethylacetate.

$^1$H NMR: δ=0.51 (s, 3H), 0.85 (d, 3H), 1.19 (t, 3H)i 1.22 (s, 3H), 1.23 (s, 3H), 1.10–2.10 (m, 21H), 2.31 (dd, 1H), 2.60 (dd, 1H), 2.85 (dd, 1H), 3.19 (m, 1H), 3.49 (m, 2H), 4.23 (m, 1H), 4.43 (m, 1H), 5.00 (m, 1H), 5.33 (m, 1H), 6.02 (d, 1H), 6.39 (d, 1H).

Example 3

1(S),3(R)-Dihydroxy-20 (R)-(4-ethyl-4-hydroxy-1-methoxy-1-hexyl)-9,10-seco-pregna-5(Z),7(E),-10 (19)-triene: isomer A (Compound 103)

Method: General Procedure 5.

Starting material IV: Compound 403.

Chromatography eluant: 50% to 0% pet.ether in ethylacetate.

$^1$H NMR: δ=0.52 (s, 3H), 0.86 (m, 9H), 1.20–2.10 (m, 25H), 2.32 (dd, 1H), 2.60 (dd, 1H), 2.85 (m, 1H), 3.16 (m, 1H), 3.34 (s, 3H), 4.23 (m, 1H), 4.43 (m, 1H), 5.00 (m, 1H), 5.33 (m, 1H), 6.02 (d, 1H), 6.38 (d, 1H).

Example 4

1(S),3(R)-Dihydroxy-20(R)-(5-hydroxy-1-methoxy-5-methyl-1-hexyl)-9,10-seco-pregna-5(Z),7(E),10 (19)-triene: isomer A (Compound 104)

Method: General Procedure 5.

Starting material IV: Compound 404.

Chromatography eluant: 50% to 0% pet.ether in ethylacetate.

$^1$H NMR: δ=0.52 (s, 3H), 0.83 (d, 3H), 1.22 (s, 6H), 1.20–2.10 (m, 23H), 2.32 (dd, 1H), 2.60 (dd, 1H), 2.85 (m, 1H), 3.20 (m, 1H), 3.34 (s, 3H), 4.23 (m, 1H), 4.43 (m, 1H), 5.00 (m, 1H), 5.33 (m, 1H), 6.02 (d, 1H), 6.38 (d, 1H).

Example 5

1(S),3(R)-Dihydroxy-20(R)-(5-ethyl-5-hydroxy-1-methoxy-1-heptyl)-9,10-seco-pregna-5(Z),7(E),-10 (19)-triene; isomer A (Compound 105)

Method: General Procedure 5.

Starting material IV: Compound 405.

Chromatography eluant: 50% to 0% pet.ether in ethylacetate.

$^1$H NMR: δ0.52 (s, 3H), 0.82 (d, 3H), 0.86 (t, 6H), 1.46 (q, 4H), 1.20–2.15 (m, 23H), 2.31 (dd, 1H), 2.60 (dd, 1H), 2.84 (m, 1H), 3.20 (m, 1H), 3.33 (s, 3H), 4.23 (m, 1H), 4.43 (m, 1H), 5.00 (m, 1H), 5.33 (m, 1H), 6.02 (d, 1H), 6.38 (d, 1H).

Example 6

1(S),3(R)-Dihydroxy-20 (R)-(1-ethoxy-5-ethyl-5-hydroxy-1-heptyl)-9,10-seco-pregna-5(Z),7(E),-10 (19)-triene: isomer A (Compound 106)

Method: General Procedure 6.

Starting material IV: Compound 406.

Chromatography eluant: 50% to 0% pet.ether in ethylacetate.

$^1$H NMR: δ=0.51 (s, 3H), 0.83 (d, 3H), 0.86 (t, 6H), 1.18 (t, 3H), 1.46 (q, 4H), 1.15–2.15 (m, 23H), 2.31 (dd, 1H), 2.60 (dd, 1H), 2.85 (m, 1H), 3.23 (m, 1H), 3.48 (m, 2H), 4.23 (m, 1H), 4.43 (m, 1H), 5.00 (m, 1H), 5.33 (m, 1H), 6.02 (d, 1H), 6.38 (d, 1H).

Example 7

1(S),3 (R)-Dihydroxy-20(R)-(6-ethyl-6-hydroxy-1-methoxy-1-octyl)-9.10-seco-pregna-5(Z),7(E),-10(19)-triene: isomer A (Compound 107)

Method: General Procedure 6.

Starting material IV: Compound 407.

Chromatography eluant: 50% to 0% pet.ether in ethylacetate.

$^1$H NMR: δ=0.52 (s, 3H), 0.82 (d, 3H), 0.86 (t, 6H), 1.46 (q, 4H), 1.15–2.10 (m, 25H), 2.31 (dd, 1H), 2.60 (m, 1H), 2.84 (m, 1H), 3.21 (m, 1H), 3.33 (s, 3H), 4.23 (m, 1H), 4.43 (m, 1H), 5.00 (m, 1H), 5.33 (m, 1H), 6.02 (d, 1H), 6.38 (d, 1H).

Example 8

1(S),3 (R)-Dihydroxy-20 (R)-(1-ethoxy-6-ethyl-6-hydroxy-1-octyl)-9,10-seco-pregna-5(Z),7(E),-10(19)-triene: isomer A (Compound 108)

Method: General Procedure 6.

Starting material IV: Compound 408.

Chromatography eluant: 50% to 0% pet.ether in ethylacetate.

$^1$H NMR: δ=0.51 (5, 3H), 0.82 (d, 3H), 0.85 (t, 6H), 1.18 (t, 3H), 1.46 (q, 4H), 1.10–2.10, (m, 25H), 2.31 (dd, 1H), 2.60 (dd, 1H), 2.84 (m, 1H), 3.22 (m, 1H), 3.47 (q, 2H), 4.23 (m, 1H), 4.43 (m, 1H), 5.00 (m, 1H), 5.33 (m, 1H), 6.02 (d, 1H), 6.38 (d, 1H).

Example 9

(S),3(R)-Dihydroxy-20(R)-(1-ethoxy-5-hydroxy-5-methyl-1-hexyl)-9, 1 0-seco-pregna-5(Z),7 (E),-10(19)-triene: isomer A (Compound 110)

Method: General Procedure 5.

Starting material IV: Compound 410.

Chromatography eluant: 50% to 0% pet.ether in ethylacetate.

$^{13}$C NMR: 147.7, 143.0, 133.2, 124.8, 117.0, 111.7, 83.1, 71.0, 70.7, 66.7, 64.5, 55.7, 50.6, 46.4, 45.2, 44.1, 42.9, 39.2, 34.9, 31.4, 29.4, 29.2, 29.1, 24.9, 23.5, 22.3, 21.3, 15.8, 13.2, 12.9

Example 10

1(S),3(R)-Dihydroxy-20 (R)-(6-hydroxy-1-methoxy-6-methyl-1-heptyl)-9,10-seco-pregna-5(Z),7(E),10(19)-triene: isomer A (Compound 111)

Method: General Procedure 5.

Starting material IV: Compound 411.

Chromatography eluant: 50% to 0% pet.ether in ethylacetate.

$^{13}$C NMR: 147.7, 143.1, 133.0, 124.9, 117.0, 111.8, 83.8, 71.0, 70.8, 66.8, 56.7, 55.8, 51.2, 46.1, 45.3, 44.0, 42.9, 39.6, 35.4, 30.3, 29.3, 29.2, 29.1, 27.0, 25.8, 24.7, 23.5, 22.2, 12.8, 12.6

Example 11

(S),3 (R)-Dihydroxy-20 (R)-(1-ethoxy-6-hydroxy-6-methyl-1-heptyl)-9. 1 0-seco-pregna-5(Z),7(E),10(19)-triene: isomer A (Compound 112)

Method: General Procedure 5.

Starting material IV: Compound 412.

Chromatography eluant: 50% to 0% pet.ether in ethylacetate.

$^1$H NMR: δ=6.38 (d, 1H), 6.01 (d, 1H), 5.33 (m, 1H), 5.00 (m, 1H), 4.43 (m, 1H), 4.23 (m, 1H), 3.48 (q, 2H), 3.22 (m, 1H), 2.84 (dd, 1H), 2.60 (dd, 1H), 2.32 (dd, 1H), 2.08–1.09 (m, 25H), 1.21 (s, 6H), 1.18 (t, 3H), 0.82 (d, 3H), 0.51 (s, 3H)

Example 12

1(S),3(R)-Dihydroxy-20(R)-(4-hydroxy-4--methyl-1-n-propoxy-1-pentyl)-9.1 0-seco-pregna-5(Z),7(E),10(19)-triene: isomer A (Compound 114)

Method: General Procedure 5.

Starting material IV: Compound 414.

Chromatography eluant: 50% to 0% pet.ether in ethylacetate.

$^1$H NMR: δ=6.39 (d, 1H), 6.02 (d, 1H), 5.33 (m, 1H), 5.00 (m, 1H), 4.43 (m, 1H), 4.23 (m, 1H), 3.38 (m, 2H), 3.19 (m, 1H), 2.84 (dd, 1H), 2.60 (dd, 1H), 2.32 (dd, 1H), 2.10–1.13 (m, 23H), 1.22 (s, 6H), 0.92 (t, 3H), 0.85 (d, 3H), 0.51 (s, 3H)

Example 13

1(S),3 (R)-Dihydroxy-20 (R)-(1-benzyloxy-4-hydroxy-4-methyl-1-pentyl)-9,10-seco-pregna-5(Z),7(E),10(19)-triene: isomer A (Compound 115)

Method: General Procedure 5.

Starting material IV: Compound 415

Chromatography eluant: 50% to 0% pet.ether in ethylacetate.

$^1$H NMR: δ=7.41–7.23 (m, 5H), 6.38 (d, 1H), 6.02 (d, 1H), 5.33 (m, 1H), 5.00 (m, 1H), 4.53 (m, 2H), 4.43 (m, 1H), 4.23 (m, 1H), 3.42 (m, 1H), 2.83 (dd, 1H), 2.60 (dd, 1H), 2.31 (dd, 1H), 2.11–1.13 (m, 21H), 1.22 (s, 6H), 0.90 (d, 3H), 0.53 (s, 3H)

Example 14

1(S),3(R)-Dihydroxy-20(R)-(4-hydroxy-4--methyl-1-phenoxythiocarbonyloxy-1-pentyl)-9,10-seco-pregna-5(Z),7(E),10(19)-triene; isomer A (Compound 116)

Method: General Procedure 6.

Starting material IV: Compound 416.

Chromatography eluant: 50% to 0% pet.ether in ethylacetate.

$^1$H NMR: δ=7.42 (t, 2H), 7.29 (t, 1H), 7.08 (d, 2H), 6.39 (d, 1H), 6.03 (d, 1H), 5.34 (t, 1H), 5.24 (m, 1H), 5.01 (m, 1H), 4.44 (m, 1H), 4.24 (m, 1H), 2.85 (dd, 1H), 2.61 (dd, 1H), 2.32 (dd, 1H), 2.15–1.20 (m, 21H), 1.26 (s, 6H), 0.97 (d, 3H), 0.54 (s, 3H)

Example 15

1(S),3(R)-Dihydroxy-20(R)-(1-methoxy-4-hydroxy-4-methyl-1-pentyl)-9.10-seco-pregna-5(Z),7(E),10(19)-triene: isomer B (Compound 121)

Method: General Procedure 5.

Starting material IV: Compound 421.

Chromatography eluant: 50% to 0% pet.ether in ethylacetate.

$^1$H NMR: δ=6.38 (d, 1H), 6.03 (d, 1H), 5.34 (m, 1H), 5.00 (m, 1H), 4.44 (m, 1H), 4.24 (m, 1H), 3.32 (s, 3H), 3.30 (m, 1H), 2.84 (m, 1H), 2.61 (dd, 1H), 2.32 (dd, 1H), 2.16 (s, 1H), 2.09–1.11 (m, 20H), 1.22 (s, 3H), 1.21 (s, 3H), 0.82 (d, 3H), 0.60 (s, 3H)

Example 16

Capsules containing Compound 101

Compound 101 was dissolved in arachis oil to a final concentration of 1 µg of Compound 101/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 µl of Compound 101 in oil solution, such that each capsule contained 0.1 pg of Compound 101.

Example 17

Dermatological Cream Containing Compound 102

In 1 g almond oil was dissolved 0.05 mg of Compound 102. To this solution was added 40 g of mineral oil and 20 g of self-emulsifying beeswax. The mixture was heated to liquify. After the addition of 40 ml hot water, the mixture was mixed well. The resulting cream contains approximately 0.5 µg of Compound 102 per gram of cream.

The following scientific articles and references have been cited throughout this application and the entire contents of each article or reference is hereby incorporated by reference.

SCIENTIFIC ARTICLES AND REFERENCES

1. Chaney, S. G. in *Textbook of Biochemistry* (Ed. Devlin, T. M), 3. Ed., Wiley-Liss, New York, 1992, pp. 1121–1124.
2. DeLuca, H. F.; Krisinger, J.; Darwish, H. *Kidney Int.* 1990, 38 (Suppl. 29), S2–S8.
3. Bouillon, R.; Okamura, W. H.; Norman, A. W. *Endocrine Rev.* 1995, 16, 200–257.
4. Colston, K. W. *Endocr. Rel. Cancer* 1995, 2, 187–201.
5. Abe, E.; Miyaura, C.; Sakagami, H.; Takeda, M.; Konno, K.; Yamazaki, T.; Yoshiki, S.; Suda, T. *Proc. Natl. Acad. Sci. U.S.A.* 1981, 78, 4990–4994.
6. Muller, K.; Svenson, M.; Bendtzen, K. *Immunol. Lett.* 1988, 17, 361–366.
7. Lind, L.; Wengle, B.; Ljunghall, S. *Acta Med. Scand.* 1987, 222, 423–427.
8. Inomata, S.; Kadowaki, S.; Yamatani, T.; Fukase, M.; Fujita, T. *Bone Miner.* 1986, 1, 187–192.
9. Editorial, *Lancet* 1989, i, p. 478.
10. Malloy, V. L. et al., *Tricontinental Meeting for Investigative Dermatology, Washington,* 1989.
11. Bikle, D. D.; *Endocr. Rev. Monogr.* 1995, 4, 77–83.
12. Carswell, S. *Exp. Neurol.* 1993, 124, 36–42.
13. Oikawa, T.; Hirotani, K.; Ogasawara, H.; Katayama, T.; Nakamura, O.; Iwaguchi, T.; Hiragun, A. *Eur. J. Pharmacol.* 1990, 178, 247–250.
14. Studzinski, G. P.; McLane, J. A.; Uskokoviç, M. R. *Critical Revs. Eukar. Gene Express.* 1993, 3, 279–312.
15. Binderup, L.; Bramm, E. *Biochem. Pharmacol.* 1988, 37, 889–895.
16. Kragballe, K. *Pharmacol. Toxicol.* 1995, 77, 241–246.
17. Highton, A.; Quell, J.; and The Calcipotriene Study Group *J. Am. Acad. Dermatol.* 1995, 32, 67–72.
18. Binderup, L.; Latini S.; Binderup, E.; Bretting, C.; Calverley, M.; Hansen, K. *Biochem. Pharmacol.* 1991, 42, 1569–1575.
19. Bikle, D. D.; *Endocr. Rev.* 1992, 13, 765–784.
20. Pols, H. A. P.; Birkenhäger J. C.; van Leeuwen, J. P. T. M. *Clin. Endocr.* 1994, 40, 285–291.
21. Calverley, M. J.; Jones, G., "Vitamin D", in *Antitumor Steroids*; (Ed. Blickenstaff, R. T.); Academic Press: San Diego, 1992, pp.193–270.
22. Binderup, L. *Biorg. Med. Chem. Lett.* 1993, 3, 1891–1896.
23. Jung, S. J.; Lee, Y. Y.; Pakkala, S.; de Vos, S.; Elstner, E.; Norman, A. W.; Green, J.; Uskokovic, M.; Koeffler, H. P. Leukem. Res. 1994, 18, 453463.
24. Mathiasen, I. S.; Colston, K. W.; Binderup, L. *J. Steroid Biochem. Mol. Biol.* 1993, 46, 365–371.
25. Colston, K. W.; Mackay, A. G.; James, S. Y.; Binderup, L.; Chander, S.; Coombes, R. C. *Biochem. Pharmacol.* 1992, 44, 2273–2280.
26. Binderup, L. *International Bone Forum* 1993, 52–55.
27. Binderup, L. *Biochem. Pharmacol.* 1992, 43, 1885–1892.
28. Elstner, E.; Linker-Israeli, M.; Said, J.; Umiel, T.; de Vos, S.; Shintaku, I. P.; Heber, D.; Binderup, L.; Uskokovic, M.; Koeffler, H. P. *Cancer Res.* 1995, 55, 2822–2830.
29. Rabasseda, X.; Mealy, N.; Castañer, J.; *Drugs Future,* 1995, 20, 567–571.
30. Johnson, C.; Tufveson, G. *Transplant Int.* 1994, 7, 392–397.
31. Bouillon, R.; Garmyn, M.; Verstuyf, A.; Segaert, S.; Casteels, K.; Mathieu, C. *Eur. J. Endocrinol.* 1995, 133, 7–16.
32. Schilli, M. B.; Paus, R.; Czarnetzki, B. M.; Reichrat, J. *Hautarzt* 1994, 45, 445–452.
33. Veyron, P.; Pamphile, R.; Binderup, L.; Touraine, J -L. *Transplant. Immunol.* 1993, 1, 72–76.
34. a. Bretting, C.; Mørk Hansen, C.; Rastrup Andersen, N., pp. 73–74;
    b. Grue-Sørensen, G.; Binderup, E.; Binderup, L., pp. 75–76;
    c. Calverley, M. J.; Grue-Sørensen, G.; Bretting, C.; Binderup, L., pp. 85–86;
    d. Hansen, K.; Mørk Hansen, C., pp. 95–96;
    e. Veyron, P.; Pamphile, R.; Binderup, L.; Touraine, J -L., pp. 922–929;
    in *Vitamin D*: A Pluripotent Steroid Hormone: Structural Studies, Molecular Endocrinology and Clinical Applications (Eds. Norman, A. W.; Bouillon, R.; Thomasset, M.), Walter de Gruyter, Berlin, 1994.
35. Mathieu, C.; Waer, M.; Casteels, K.; Laureys, J.; Bouillon, R. *Endocrinology* 1995, 136, 866–872.
36. Mathieu, C.; Laureys, J.; Waer, M.; Bouillon, R. *Transplant. Proc.* 1994, 26, 3128–3129.
37. Peleg, S.; Sastry, M.; Collins, E. D.; Bishop, J. E.; Norman, A. W. *J. Biol. Chem.* 1995, 270, 10551–10558.
38. a. Bretting, C.; Calverley, M. J.; Binderup, L., pp. 159–160;
    b. Hansen, K.; Calverley, M. J., Binderup, L., pp. 161–162;
    c. Calverley, M. J.; Binderup, E.; Binderup, L., pp. 163–164;
    d. Binderup, E.; Calverley, M. J.; Binderup, L., pp. 192–193;
    in *Vitamin D*: Gene Regulation, Structure-Function Analysis and Clinical Application (Eds. Norman, A. W.; Bouillon, R.; Thomasset, M.), Walter de Gruyter, Berlin, 1991.

39. Ikekawa, N., pp.25–33; in *Vitamin D*: Molecular, Cellular and Clinical Endocrinology (Eds. Norman, A. W.; Schaefer, K.; Grigoleit, H. -G.; Herrath, D. v.), Walter de Gruyter, Berlin, 1988.
40. Eguchi, T.; Yoshida, M.; ikekawa, N. Bioorg. Chem. 1989, 17, 294–307.
41. Hansen, C. M.; Mathiasen, I. S., and Binderup, L., *J. Invest. Dermatol. Symposium Proceedings* 1996, 1, 44–48.
42. Calverley, M. J. *Tetrahedron* 1987, 43, 4609–4619.

What is claimed is:

1. A compound of the formula

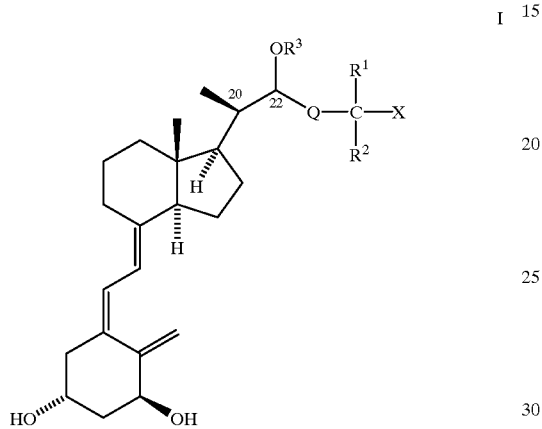

I in which formula X is hydrogen or hydroxy; $R^1$ and $R^2$, which may be the same or different, stand for hydrogen or a $C_1$–$C_3$ alkyl radical; or $R^1$ and $R^2$, taken together with the carbon atom bearing the group X, can form a $C_3$–$C_6$ carbocyclic ring; $R^3$ stands for a $C_1$–$C_3$ alkyl radical, an aryl or an aralkyl radical, or for $YR^4$, in which Y stands for the radicals —CO—S—, —CS—O— or —CS—S—, and $R^4$ stands for a $C_1$–$C_3$ alkyl radical or an aryl or an aralkyl radical; Q is $(CH_2)_n$, n being 1–4; $R^1$, $R^2$ and Q independently may optionally be substituted with one or more fluorine atoms.

2. A compound of formula I according to claim 1 in which Q is $(CH_2)n$, n being 2 or 3, in which X is hydroxy, $R^1$ and $R^2$ are methyl or ethyl, and $R^3$ is methyl or ethyl.

3. A diastereoisomer of a compound according to any one of claims 1 or 2, in pure form; or a mixture of said diastereoisomers.

4. A diastereoisomer of a compound according to claim 3 having the "R"-configuration at C-22.

5. A compound according to claim 1 which is

1(S),3 (R)-Dihydroxy-20(R)-(1-methoxy-4-hydroxy-4-methyl-1-pentyl)-9,10-seco-pregna-5(Z),7(E),10(19)-triene; isomer A, or 1(S),3(R)-Dihydroxy-20(R)-(1-ethoxy-4-hydroxy-4-methyl-1-pentyl)-9,10-seco-pregna-5(Z),7(E),10(19)-triene; isomer A.

6. A method for producing a compound of formula I of claim 1 in which a) 1(S),3(R)-bis-(tert)-butyldimethylsilyloxy)-20(R)-formyl-9,10-seco-pregna-5(E),7(E),10(19)-triene is reacted with an organometallic reagent R-Met-Hal or R-Met, in which Met is a metal, Hal is Cl, Br or I, and R is

in which X is H, OH or $OR^5$, $R^5$ being an alcohol protective group, and $R^1$, $R^2$ and Q have the above meanings, to form a mixture of two C-22-epimers IIA and IIB

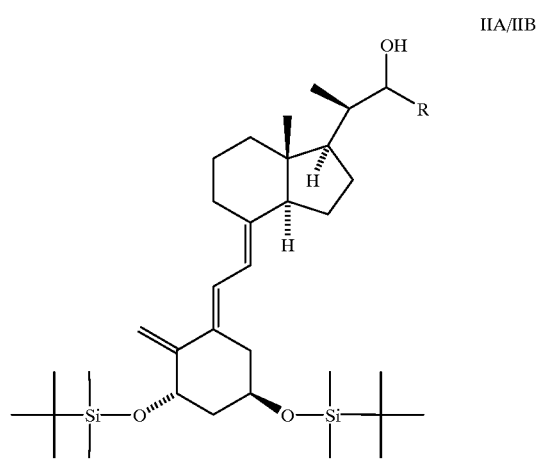

IIA/IIB which epimers are separated;

b) a compound of formula IIA or IIB of step a), is alkylated to the corresponding compound IIIA or IIIB, in which R and $R^3$ have the above meanings or optionally acylated to the corresponding compound IIIA or IIIB, where $R^3=YR^4$, Y and $R^4$ having the meanings defined in claim 1

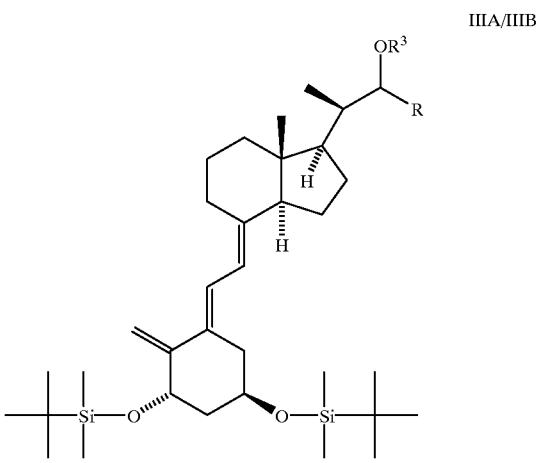

IIIA/IIIB c) a compound of formula IIIA or IIIB of step b) is isomerized to the corresponding compound IVA or IVB by means of UV-light in the presence of a triplet sensitizer,

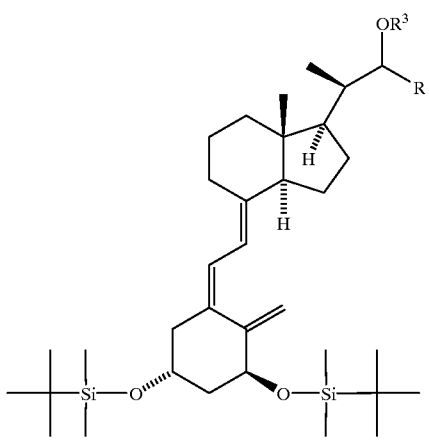

IVA/IVB in which R and $R^3$ have the above meanings;

d) a compound of formula IVA or IVB is deprotected to the corresponding compound of the general formula 1.

7. A method according to claim 6 in which steps b) and c) are performed in the reverse order.

8. A method according to claim 6 in which steps c) and d) are performed in the reverse order.

9. A pharmaceutical composition containing an effective amount of one or more of the compounds of claim 1, together with pharmaceutically acceptable carriers.

10. A pharmaceutical composition according to claim 9 in dosage unit form containing from 0.1 ppm to 0.1% by weight of the dosage unit of a compound of formula 1.

11. A method for the treatment of abnormal skin cell proliferation or for obtaining an immunosuppressive effect, said method comprising administering to a patient in need of such treatment an effective amount of a compound according to claim 1.

12. A method of treatment for inhibiting undesirable skin cell proliferation which comprises administering to a patient in need of such treatment, an effective amount of a compound according to claim 1.

* * * * *